(12) United States Patent
Myllyoja et al.

(10) Patent No.: US 11,149,206 B2
(45) Date of Patent: Oct. 19, 2021

(54) METHOD FOR CONVERTING CARBOXYLIC ACIDS AND ESTERS INTO BASE OIL HYDROCARBONS

(71) Applicant: Neste Oyj, Espoo (FI)

(72) Inventors: Jukka Myllyoja, Porvoo (FI); Mika Kettunen, Porvoo (FI); Rami Piilola, Porvoo (FI)

(73) Assignee: NESTE OYJ, Espoo (FI)

( * ) Notice: Subject to any disclaimer, the term of this patent is extended or adjusted under 35 U.S.C. 154(b) by 0 days.

(21) Appl. No.: 16/623,210

(22) PCT Filed: Jun. 15, 2018

(86) PCT No.: PCT/EP2018/065980
§ 371 (c)(1),
(2) Date: Dec. 16, 2019

(87) PCT Pub. No.: WO2018/234190
PCT Pub. Date: Dec. 27, 2018

(65) Prior Publication Data
US 2021/0139787 A1    May 13, 2021

(30) Foreign Application Priority Data

Jun. 19, 2017 (FI) ................................ 20175569
Aug. 31, 2017 (FI) ................................ 20175780
(Continued)

(51) Int. Cl.
*C10G 3/00* (2006.01)
*B01J 21/04* (2006.01)
(Continued)

(52) U.S. Cl.
CPC ............ *C10G 3/50* (2013.01); *B01D 3/143* (2013.01); *B01J 21/04* (2013.01); *B01J 21/063* (2013.01);
(Continued)

(58) Field of Classification Search
USPC .................................. 585/240; 44/307, 308
See application file for complete search history.

(56) References Cited

U.S. PATENT DOCUMENTS 8,679,805 B2   3/2014 Chung et al.
9,523,061 B2   12/2016 Nelson et al.
(Continued)

FOREIGN PATENT DOCUMENTS

CN    1867653 A    11/2006
CN    102300967 A  12/2011
(Continued)

OTHER PUBLICATIONS

Eisner, et al., "The synthesis of long-chain, branched, hydroxyaliphatic compounds", Bull. Soc. Chim., 1995, pp. 212-218.
(Continued)

*Primary Examiner* — Nina Bhat
(74) *Attorney, Agent, or Firm* — Buchanan Ingersoll & Rooney PC

(57) ABSTRACT

A number of different branched hydrocarbon compounds (formula I) having a star-like configuration (S) are prepared from renewable oils containing fatty acids or derivatives containing fatty acids. The branched hydrocarbon compounds may be isolated individually or in mixtures, and may be used as part of base oils, such as renewable base oils (RBOs). A process for preparing the branched hydrocarbon compounds of formula I involve conditions that favour a trimerisation reaction followed by hydrotreating conditions. The compounds of formula I may be made by catalytically
(Continued)

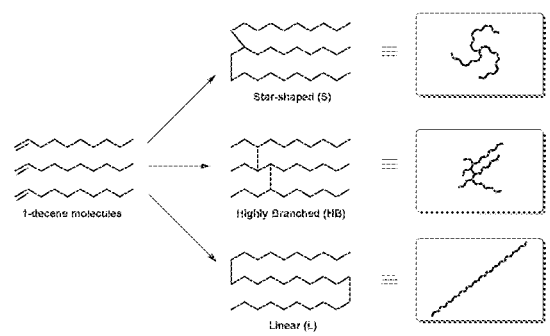

Examples of Poly-alpha-olefins from 1-decene treating renewable material in a process, and the compounds have desirable qualities relating to lubrication, cold flow as well as having a low Noack volatility.

25 Claims, 6 Drawing Sheets

(30) Foreign Application Priority Data

| Aug. 31, 2017 | (FI) | ..................................... | 20175781 |
|---|---|---|---|
| Aug. 31, 2017 | (FI) | ..................................... | 20175782 |
| Dec. 7, 2017 | (FI) | ..................................... | 20176095 |

(51) Int. Cl.

| B01J 21/06 | (2006.01) |
|---|---|
| B01J 23/883 | (2006.01) |
| B01J 35/10 | (2006.01) |
| C07C 45/41 | (2006.01) |
| C10G 45/58 | (2006.01) |
| C10L 1/08 | (2006.01) |
| B01J 29/85 | (2006.01) |
| C10G 67/02 | (2006.01) |
| C11C 1/04 | (2006.01) |
| C10M 105/04 | (2006.01) |
| C10M 105/06 | (2006.01) |
| C10M 169/04 | (2006.01) |
| B01D 3/14 | (2006.01) |
| C07C 51/44 | (2006.01) |
| C10M 177/00 | (2006.01) |
| C11C 1/10 | (2006.01) |
| C10N 30/00 | (2006.01) |
| C10N 20/00 | (2006.01) |
| C10N 30/02 | (2006.01) |
| C10N 30/04 | (2006.01) |
| C10N 30/10 | (2006.01) |
| C10N 30/12 | (2006.01) |
| C10N 30/14 | (2006.01) |
| C10N 30/16 | (2006.01) |
| C10N 70/00 | (2006.01) |

(52) U.S. Cl.
CPC ............ *B01J 23/883* (2013.01); *B01J 29/85* (2013.01); *B01J 35/1014* (2013.01); *B01J 35/1019* (2013.01); *B01J 35/1038* (2013.01); *B01J 35/1061* (2013.01); *C07C 45/41* (2013.01); *C07C 51/44* (2013.01); *C10G 3/46* (2013.01); *C10G 3/49* (2013.01); *C10G 45/58* (2013.01); *C10G 67/02* (2013.01); *C10L 1/08* (2013.01); *C10M 105/04* (2013.01); *C10M 105/06* (2013.01); *C10M 169/04* (2013.01); *C10M 177/00* (2013.01); *C11C 1/04* (2013.01); *C11C 1/10* (2013.01); *C10G 3/44* (2013.01); *C10G 2300/1003* (2013.01); *C10G 2300/1014* (2013.01); *C10G 2300/1018* (2013.01); *C10G 2300/202* (2013.01); *C10G 2300/301* (2013.01); *C10G 2300/302* (2013.01); *C10G 2300/304* (2013.01); *C10G 2300/308* (2013.01); *C10G 2300/4006* (2013.01); *C10G 2300/4012* (2013.01); *C10G 2300/4018* (2013.01); *C10G 2400/04* (2013.01); *C10G 2400/10* (2013.01); *C10L 2200/0484* (2013.01); *C10L 2270/026* (2013.01); *C10L 2290/543* (2013.01); *C10M 2203/022* (2013.01); *C10M 2203/0206* (2013.01); *C10M 2203/045* (2013.01); *C10M 2203/065* (2013.01); *C10N 2020/065* (2020.05); *C10N 2020/067* (2020.05); *C10N 2030/02* (2013.01); *C10N 2030/04* (2013.01); *C10N 2030/10* (2013.01); *C10N 2030/12* (2013.01); *C10N 2030/14* (2013.01); *C10N 2030/16* (2013.01); *C10N 2030/43* (2020.05); *C10N 2030/74* (2020.05); *C10N 2070/00* (2013.01)

(56) References Cited

U.S. PATENT DOCUMENTS

| 2005/0077208 | A1 | 4/2005 | Miller et al. | |
|---|---|---|---|---|
| 2005/0263435 | A1* | 12/2005 | Skledar | C08F 8/04 |
| | | | | 208/18 |
| 2007/0135663 | A1 | 6/2007 | Aalto et al. | |
| 2007/0161832 | A1* | 7/2007 | Myllyoja | C10M 105/04 |
| | | | | 585/7 |
| 2007/0244018 | A1* | 10/2007 | Visger | C08F 293/005 |
| | | | | 508/545 |
| 2008/0034645 | A1 | 2/2008 | Bressler | |
| 2009/0014354 | A1 | 1/2009 | Knuuttila et al. | |
| 2010/0234654 | A1* | 9/2010 | Wang | C10M 105/04 |
| | | | | 585/254 |
| 2011/0107656 | A1 | 5/2011 | Miller | |
| 2012/0220506 | A1* | 8/2012 | Qin | C10M 145/14 |
| | | | | 508/287 |
| 2013/0190544 | A1 | 7/2013 | Wang et al. | |
| 2013/0217606 | A1 | 8/2013 | Wang et al. | |
| 2014/0046104 | A1 | 2/2014 | Mcneff et al. | |
| 2014/0115955 | A1 | 5/2014 | Mcneff et al. | |
| 2014/0171703 | A1 | 6/2014 | Wang et al. | |
| 2014/0323665 | A1* | 10/2014 | Wu | C10G 69/126 |
| | | | | 525/338 |
| 2014/0335586 | A1* | 11/2014 | Zhang | C10G 3/46 |
| | | | | 435/167 |
| 2015/0018581 | A1* | 1/2015 | Kettunen | C11C 3/123 |
| | | | | 568/397 |
| 2015/0018588 | A1 | 1/2015 | Myllyoja et al. | |
| 2015/0183915 | A1* | 7/2015 | Johnson | C08F 220/18 |
| | | | | 508/469 |
| 2015/0251168 | A1 | 9/2015 | Kettunen et al. | |
| 2016/0137944 | A1 | 5/2016 | Liang et al. | |
| 2017/0088789 | A1* | 3/2017 | Grisso | C10M 157/04 |
| 2017/0240832 | A1 | 8/2017 | Hahn et al. | |
| 2017/0334806 | A1* | 11/2017 | Agee | C10M 107/04 |
| 2017/0362154 | A1 | 12/2017 | Kettunen et al. | |
| 2018/0171252 | A1* | 6/2018 | Fourage | C10M 105/04 |
| 2020/0181503 | A1 | 6/2020 | Myllyoja et al. | |
| 2020/0181504 | A1 | 6/2020 | Myllyoja et al. | |
| 2020/0181527 | A1 | 6/2020 | Kulmala et al. | |
| 2021/0139786 | A1 | 5/2021 | Toppinen et al. | |

FOREIGN PATENT DOCUMENTS

| CN | 102906229 | A | 1/2013 | |
|---|---|---|---|---|
| CN | 103773442 | A | 5/2014 | |
| DE | 102009017827 | A1 | 10/2010 | |
| DK | 2809745 | T3 | 12/2014 | |
| EP | 1741767 | A1 | 1/2007 | |
| EP | 1741768 | A1 | 1/2007 | |
| EP | 1741767 | B1 | 7/2015 | |
| EP | 2809745 | B1 | 4/2016 | |
| EP | 3012310 | A1 | 4/2016 | |
| JP | 2004124080 | A | 4/2004 | |
| WO | 00/68799 | A1 | 11/2000 | |
| WO | 2007061698 | A2 | 5/2007 | |
| WO | 2007068795 | A1 | 6/2007 | |
| WO | 2007068800 | A2 | 6/2007 | |
| WO | 2008152200 | A1 | 12/2008 | |
| WO | 2012156679 | A1 | 11/2012 | |
| WO | 2013113976 | A1 | 8/2013 | |
| WO | WO-2013113976 | A1 * | 8/2013 | ........... C07C 5/2735 |
| WO | 2014099371 | A2 | 6/2014 | |
| WO | 2014099373 | A1 | 6/2014 | |

(56) References Cited

FOREIGN PATENT DOCUMENTS

| WO | 2016061050 A1 | 4/2016 | | |
|---|---|---|---|---|
| WO | 2016062868 A1 | 4/2016 | | |
| WO | WO-2016062868 A1 * | 4/2016 | ............ | B01J 23/883 |
| WO | WO-2017001606 A1 * | 1/2017 | ............... | C12N 9/88 |

OTHER PUBLICATIONS

International Search Report (PCT/ISA/210) and Written Opinion (PCT/ISA/237) dated Jul. 19, 2019, by the European Patent Office as the International Searching Authority for International Application No. PCT/EP2018/065980.
Rush, et al., "Generation of unusual branched long chain alkanes from hydrous pyrolysis of anamox bacterial biomass", Organic Geochemistry, 2014, vol. 76, pp. 136-145.
Tamai, et al., "Estimation of flow activation volume of synthetic ester lubricants", J. Japan Petrol. Inst., 1982, vol. 25, No. 5, pp. 281-285.
Toubiana, et al., "Long-chain aliphatic substances related to bacterial lipids", Ann. Chim., 1962, vol. 7, pp. 593-642.
Deffense Etienne, "From Organic Chemistry to Fat and Oil Chemistry", OCL, vol. 16, No. 1, 2009, pp. 14-24.
International Preliminary Report on Patentability received for PCT Application No. PCT/EP2018/065971, dated Jan. 2, 2020, 8 pages.
International Preliminary Report on Patentability received for PCT Application No. PCT/EP2018/065973, dated Jan. 2, 2020, 7 pages.
International Search Report (PCT/ISA/210) and Written Opinion (PCT/ISA/237) received for PCT Application No. PCT/EP2018/065978, dated Sep. 13, 2018, 16 pages.
International Search Report (PCT/ISA/210) and Written Opinion (PCT/ISA/237) received for PCT Application No. PCT/EP2018/065971, dated Jul. 19, 2018, 10 pages.
International Search Report and Written Opinion received for PCT Application No. PCT/EP2018/065973, dated Jul. 19, 2018, 9 pages.
International Search Report (PCT/ISA/210) and Written Opinion (PCT/ISA/237) received for PCT Application No. PCT/EP2018/065976, dated Aug. 27, 2018, 11 pages.
Non Final Office Action dated Nov. 5, 2020, by the U.S. Patent and Trademark Office in U.S. Appl. No. 16/623,257, 8 pages.
Restriction Requirement dated Jan. 28, 2021, by the U.S. Patent and Trademark Office in U.S. Appl. No. 16/623,276, 7 pages.
Non Final Office Action dated Jan. 6, 2021, by the U.S. Patent and Trademark Office in U.S. Appl. No. 16/623,306, 16 pages.
Non Final Office Action dated Mar. 31, 2021, by the U.S. Patent and Trademark Office in U.S. Appl. No. 16/623,188, 10 pages.
First Office Action dated Jul. 2, 2021, by the Chinese Patent Office in corresponding Chinese Patent Application No. 201880039835.4, and an English Translation of the Office Action. (7 pages).
Notice of Allowance dated Jul. 6, 2021, by the U.S. Patent and Trademark Office in U.S. Appl. No. 16/623,306.
Notice of Allowance dated Jul. 15, 2021, by the U.S. Patent and Trademark Office in U.S. Appl. No. 16/623,257.
Notice of Allowance dated Jul. 12, 2021, by the U.S. Patent and Trademark Office in U.S. Appl. No. 16/623,188.
Office Action dated Jul. 2, 2021, by the U.S. Patent and Trademark Office in U.S. Appl. No. 16/623,276.

* cited by examiner

Figure 1 – Examples of Poly-alpha-olefins from 1-decene
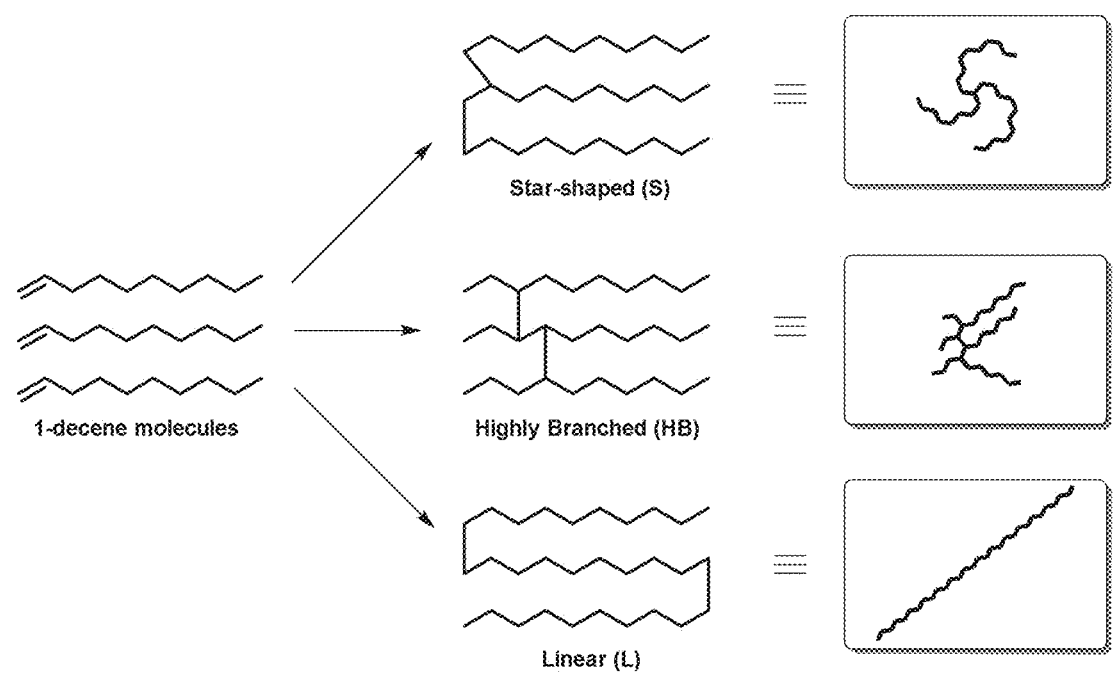

Figure 2 – Scheme for producing trimer
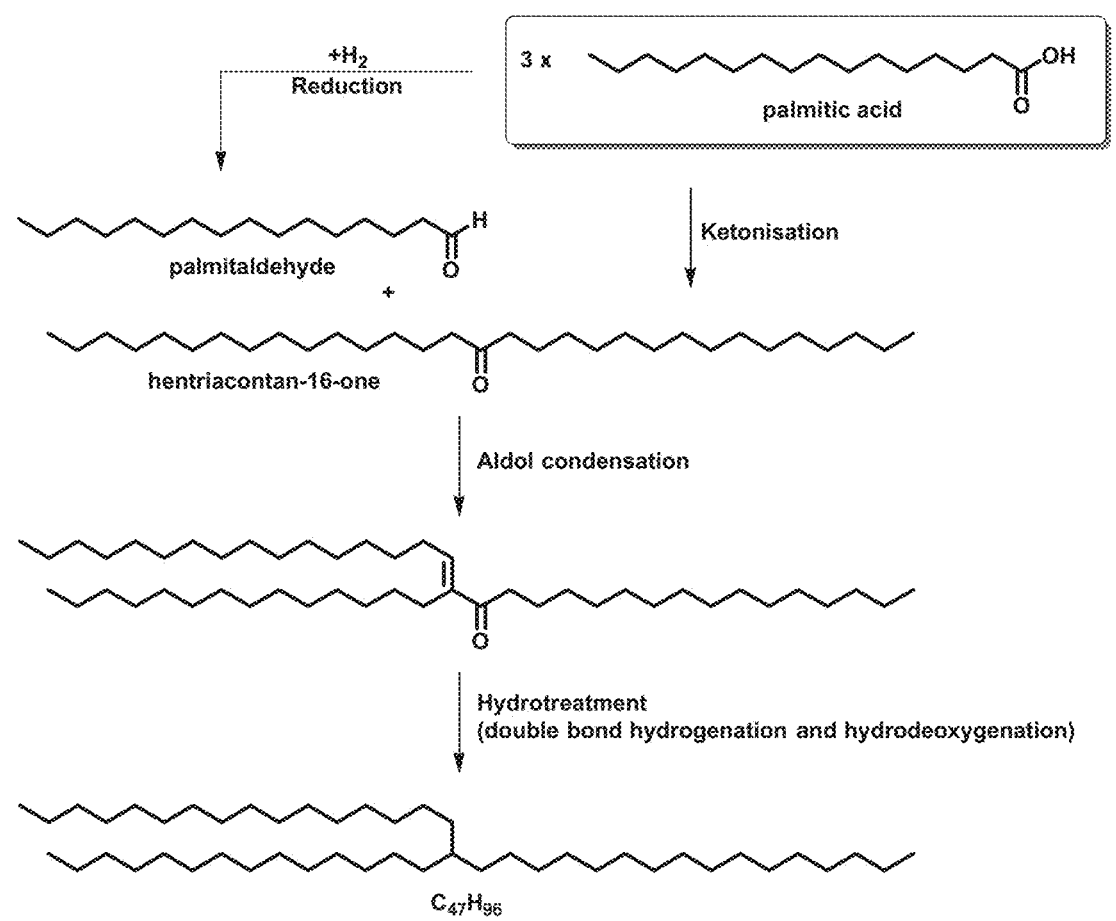

Figure 3 – Trimerised palmitic acid (C16:0 fatty acid)
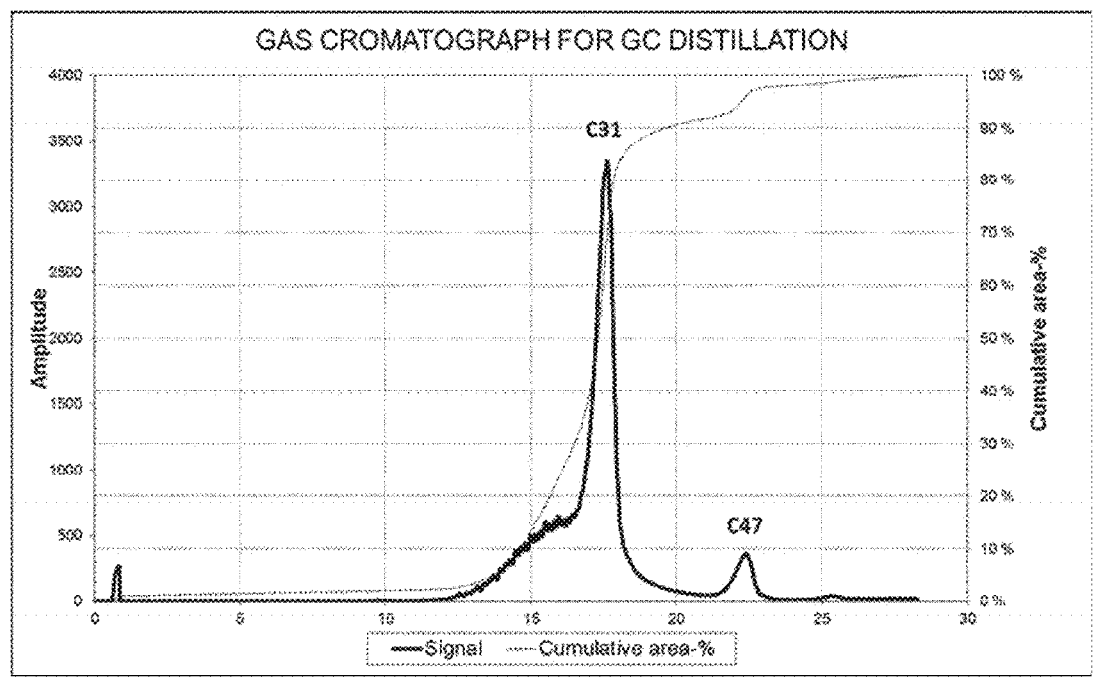
Figure 4 – Trimerised palm fatty acid distillate (PFAD) (C16/C18 fatty acids)
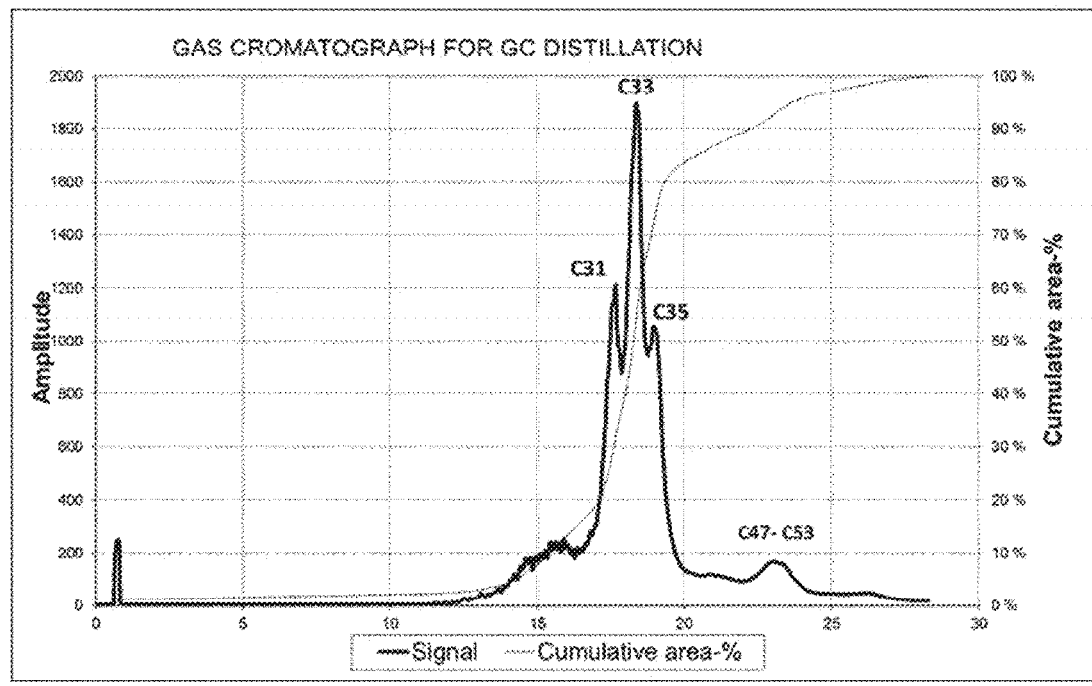

Figure 5 – Trimers as function of fatty acid conversion
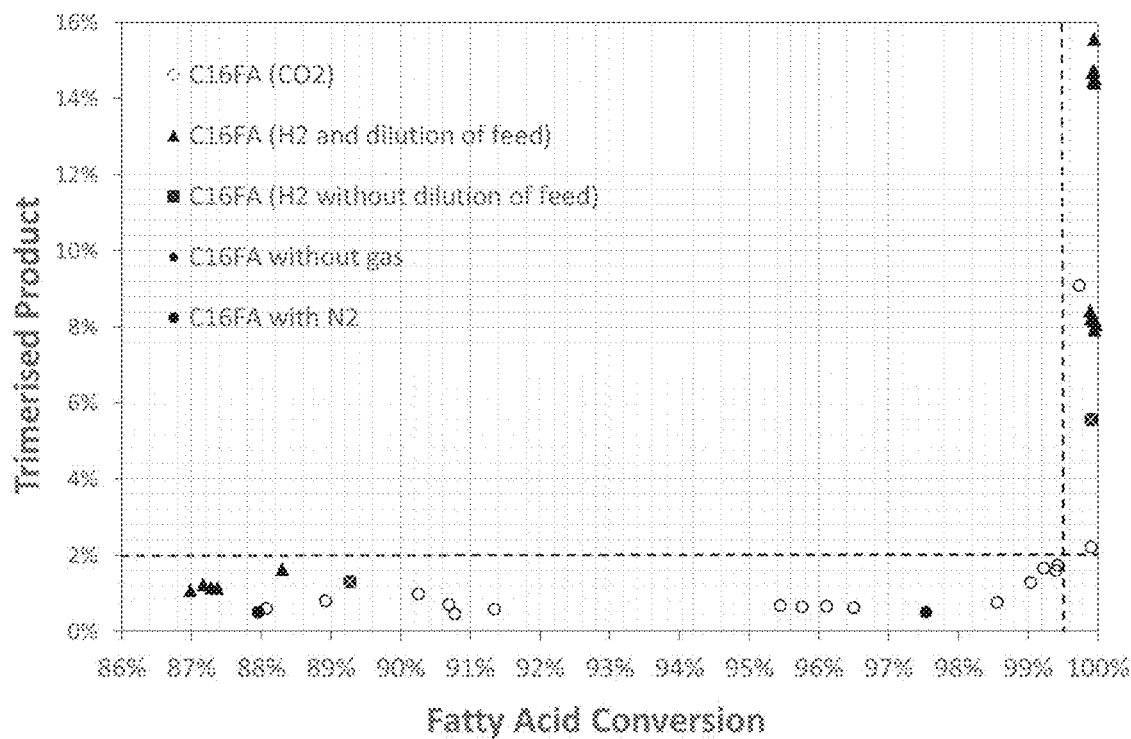
Figure 6 – Expansion of figure 5
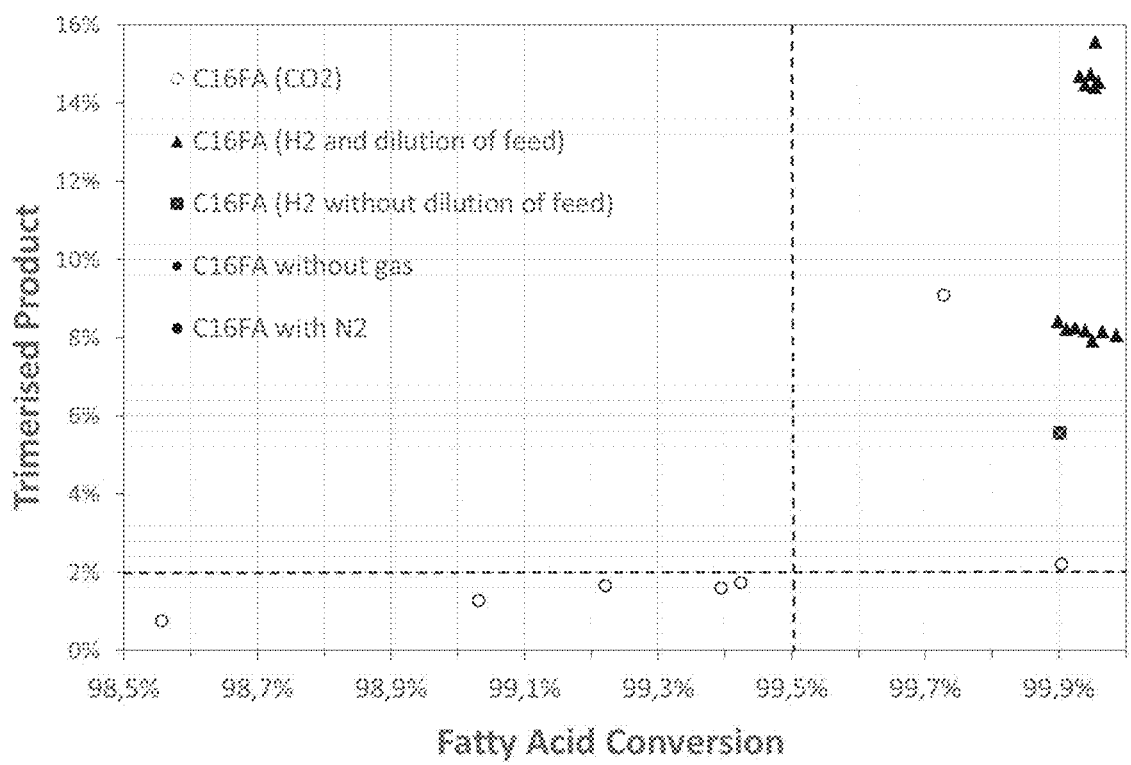

Figure 7 – Trimerised Palmitic acid (C16:0) fraction boiling over 450 °C
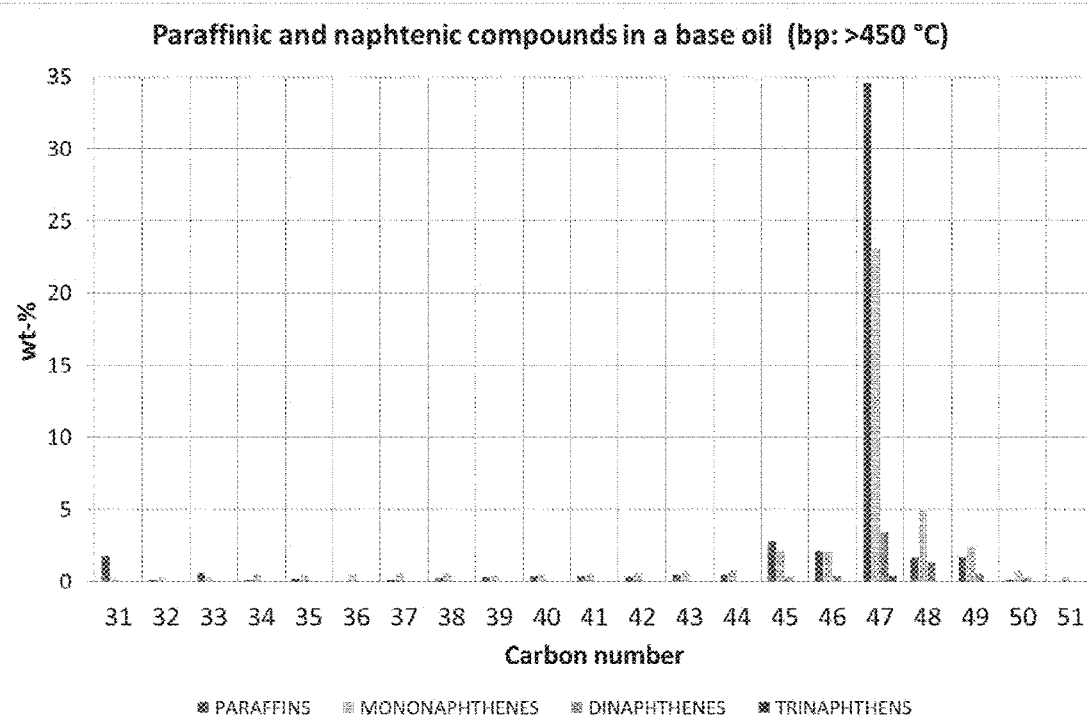
Figure 8 – Trimerised Palmitic acid (C16:0) fraction boiling 380 - 450 °C
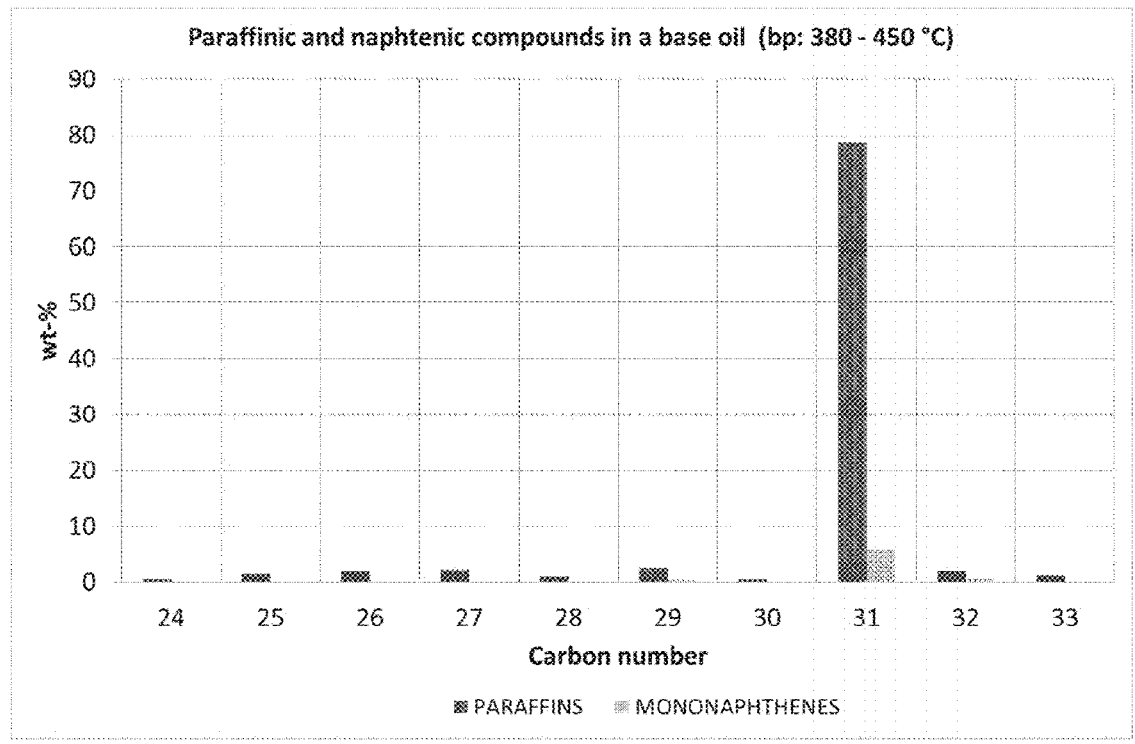

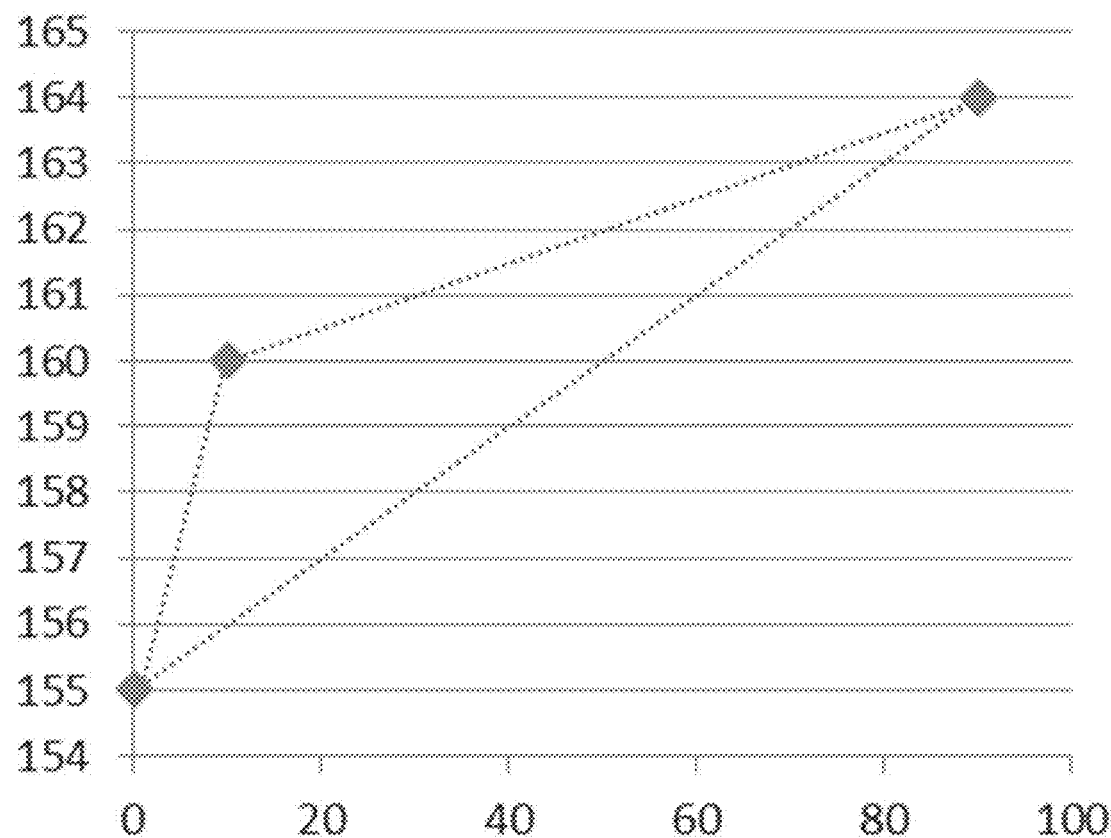
Figure 9 – Viscosity index of base oil of table 6 and 8 isomerised at 312 °C

METHOD FOR CONVERTING CARBOXYLIC ACIDS AND ESTERS INTO BASE OIL HYDROCARBONS

TECHNICAL FIELD

The present invention relates to the field of renewable base oils (RBO), in particular novel base oil compounds displaying superior lubrication properties, and their intermediates, base oil mixtures comprising superior lubrication properties and processes for base oil production from a renewable feed, base oil compositions obtainable therefrom, and uses of the renewable base oil compositions of the present invention for improving the lubricating properties of base oil.

BACKGROUND ART

Fluid film lubrication is important in order to reduce friction between surfaces in proximity and moving relative to each other. Without lubrication or with insufficient lubrication such friction will lead to increased heat and wear.

Base oils are used to manufacture products including lubricants, motor oil and metal processing fluids. One of the most important factors in the base oil is the viscosity at various temperatures.

Synthetic oil base stocks such as the poly-alpha-olefins may be prepared by polymerising alpha-olefins, such as shown in FIG. 1 with 1-decene With reference to FIG. 1, poly-alpha olefins may—depending on the reaction conditions—result in linear hydrocarbons (L), highly branched hydrocarbons (HB) or the highly coveted star-shaped (S) configuration. The star-shaped orientation cannot be obtained from regular isomerisation reactions of linear hydrocarbons, which typically results in short methyl branches. It displays superior lubrication properties, such as high viscosity index compared to the highly branched or linear molecules, and is also for that reason desirable as a base oil.

WO 2013/113976 A1 (to Neste Oil Oyj) discloses a method for producing base oil components by reacting a feed containing fatty acids and derivatives thereof with a dual catalyst system, such as NiMo and $K_2O/TiO_2$ on a support under hydrogen pressure. The reactions involve a ketonisation reaction that dimerises fatty acids that is subsequently hydrodeoxygenated into linear hydrocarbons. This dimerization reaction produces linear (L) base oils (see for example claim 2 of WO 2013/113976 A1).

WO 2014/099371 A2 (to ExxonMobil Research and Engineering Company) discloses a process for making saturated hydrocarbons from renewable feeds in which an acidic catalyst dimerises two unsaturated fatty acids on a triglyceride backbone through double bond dimerization followed by hydrotreatment. Using the double bonds of the fatty acids to dimerise triglycerides result in highly branched (HB) hydrogenated dimers, such as i-$C_{34}H_{70}$ (see for example FIG. 1 of WO 2014/099371 A2).

WO 2014/099373 A1 (to ExxonMobil Research and Engineering Company) discloses a process for making lube base stocks from renewable feeds. FIG. 3 of WO 2014/099373 A1 discloses a ketonisation between a triglyceride and citric acid followed by hydrotreatment. This result in a poly-alpha-olefin (PAO) like structure with star-shaped (S) orientation. Here the PAO like structure is obtained by using a citric acid scaffold to guide the ketonisation reactions between two carboxylic acids in order to obtain a star-shaped (S) configuration. FIGS. 3 and 7 of WO 2014/099373 contain errors in the structures; no enabling disclosures of those structures are disclosed. In particular the star shaped molecules according to the present invention cannot and have not been made in WO 2014/099373.

In view of the prior art cited above there is a further need for renewable base oil components with good lubrication properties and processes to prepare such renewable base oils. In particular there is a further need for renewable base oil components similar to the poly-alpha-olefin (PAO) type with star-shaped orientation, which displays superior lubrication properties, as well as other beneficial properties.

SUMMARY OF INVENTION

The present invention was made in view of the prior art described above, and the object of the present invention is to provide novel base oil compounds with star-shaped orientations, in particular processes for obtaining base oil mixtures having good lubricity properties, such as a high viscosity index, including base oil compounds with a star-shaped orientations.

To solve the problem, the present invention provides compounds of the formula I,

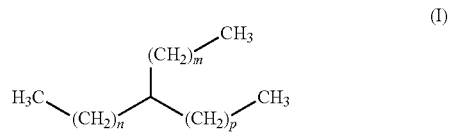

where n, m and p are independently of each other an integer value between 9 and 41, such as an odd numbered integer value, and where the total carbon number of formula I is between 31 and 65. The selection of n, m and p of formula I may be subject to one or more provisos, such that when n and m are both 9, then p is not 9 or 11, and with the proviso that n, m and p are not all 11.

In particular n, m and p may independently of each other be an odd numbered integer value between 9 and 41, where the total carbon number of formula I is between 31 and 65, with the proviso that when n and m are both 9, then p is not 9 or 11, and with the proviso that n, m and p are not all 11.

The selection of n, m and p of formula I may be where n is 13 or 15; m and p are independently of each other either 15 or 17.

That is, the inventors of the present invention in a first aspect of the invention found that these novel compounds with a star orientation having good lubricity properties, such as a high viscosity index, may be formed from one or more trimerisation reactions, such as by one reaction scheme where two fatty acids react under ketonisation conditions leading to a ketone and a condensation reaction, where one of the alpha-carbon atoms of the ketone reacts with a fatty acid to form intermediate compounds of the formula II,

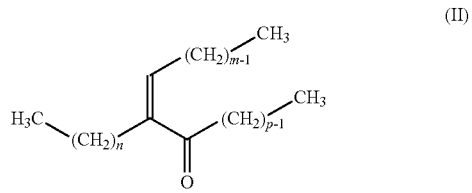

where n, m and p are independently of each other an integer value between 9 and 41, and where the total carbon number of formula II is between 31 and 65.

The selection of n, m and p of formula II may be where n is 13 or 15; m and p are independently of each other either 15 or 17.

Formula II may undergo hydrogenation reactions, such as double bond hydrogenation and hydrodeoxygenation to yield formula I.

The fatty acids used to prepare compounds of formula I or II may for example be $C_{16}$ fatty acids, $C_{18}$ fatty acids or mixtures thereof. Compounds of formula II, where n is 13; m and p are both 15 may be prepared exclusively from $C_{16}$ fatty acids, and compounds of formula I, where n is 13; m and p are both 15 may be prepared exclusively from $C_{16}$ fatty acids.

The compounds of formula I may be isomerised to produce isomerised star-shaped compounds obtainable by subjecting one or more compounds of formula I to an isomerisation step. The isomerised star-shaped compounds obtained from a process of isomerising star-shaped compounds may comprise one or more methyl branches, such as between 1 to 5 methyl branches. It is advantageous to provide isomerisation conditions that avoid or reduce cracking to the extent that one of the three branches forming the star polymer is lost or reduced to a methyl, ethyl or propyl branch.

Compounds of formula I may be present in a base oil mixture comprising one or more compound(s) of formula I, wherein n, m and p are independently of each other an integer value, such as an odd numbered integer value, between 9 and 41, and where the total carbon number of formula I is between 31 and 65.

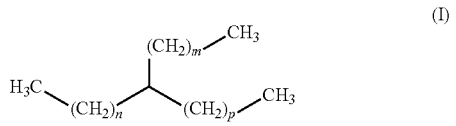

(I)

The base oil mixture may comprise one or more compound(s) of formula I, wherein n is 13 or 15; m and p are independently of each other either 15 or 17.

The base oil mixture may comprise a compound of formula I, wherein n is 13; m and p are both 15.

The base oil mixture may have a boiling point of 380° C. or more, such as 450° C. or more.

The base oil mixture may comprise at least 2%, such as at least 5%, such as at least 10% or more of the one or more compound(s) of formula I.

The base oils may be produced by a process for base oil production, comprising a) trimerising a feed comprising at least one fatty acid to provide a trimerisation product where a mixture of fatty acid trimers is obtained; and b) hydrotreating at least a portion of the trimerisation product to provide a base oil product; where the hydrotreated base oil product comprises one or more compound(s) of formula I, wherein n, m and p are independently of each other an integer value between 9 and 41, and where the total carbon number of formula I is between 31 and 65;

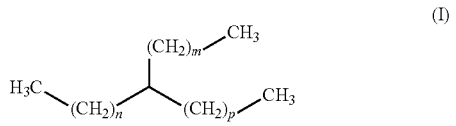

(I)

The process may be characterised in the hydrotreated base oil product having a pour point lower than 5° C.

The process may be characterised in that carbon atoms of one or more compound(s) of formula I exclusively come from monocarboxylic fatty acids.

The process may be further characterised in that the trimerisation is carried out until 99.5% of the at least one fatty acids have been converted.

The process may be further characterised in that the trimerisation is carried out at a conversion level of at least 99.5% of the at least one fatty acid of the feed.

The process may be further characterised in that the trimerisation is carried out until at least 5% trimer product has been formed.

The process may be further characterised in that where the base oil comprises at least partly the trimerisation product of formula I.

The process may be further characterised in that it either does or does not include a step for isomerising the trimerisation product.

The process may further under step a) comprise contacting the at least one fatty acid with a trimerisation catalyst in in a trimerisation zone under trimerisation conditions to provide the mixture of fatty acid trimers; and step b) comprises contacting the mixture of fatty acid trimers with a hydrotreating catalyst in the presence of hydrogen gas in a hydrotreating zone under hydrotreating conditions to provide the base oil product.

The trimerisation conditions may comprise a temperature in the range from 300 to 400° C., a pressure in the range from 5 to 100 barg and a WHSV in the range from 0.1-5 h$^{-1}$, and the trimerisation catalyst comprises a metal oxide catalyst.

The trimerisation catalyst may comprise a catalyst selected from one or more of the list consisting of: Ti, Mn, Mg, Ca containing metal oxide catalyst; preferably the trimerisation catalyst is a Ti containing metal oxide catalyst. For example, the trimerisation catalyst may comprise $TiO_2$ and one or more alkali metal oxides, preferably where the one or more alkali metal oxides are selected from one or more of the list consisting of: Li, Na, K containing metal oxide(s).

Trimerising under step a) of the process may comprise the formation of a ketone from a reaction between two fatty acids followed by a condensation reaction between the ketone and another fatty acid to produce an alpha-substituted and alpha-unsaturated ketone.

In the process, the at least one fatty acid may be selected from a $C_9$ to $C_{22}$ fatty acid.

In the process, the feed comprising at least one fatty acid may be selected from one or more of the list consisting of: palm oil, canola oil, rapeseed oil, olive oil, sunflower oil, beef fat, lard, coconut oil, corn oil, soybean oil, jatropha oil, tall oil, crude tall oil, tall oil pitch, tall oil fatty acids, tall oil heads.

In the process, the feed comprising at least one fatty acid may be diluted with a stream of hydrocarbons, or where the trimerisation product is diluted with a stream of hydrocarbons. The stream of hydrocarbons may be recycled product of the process, for example the ratio of feed comprising at least one fatty acid to recycled product of the process is between 1:9 and 9:1. The feed comprising at least one fatty acid may also be diluted with a stream of product withdrawn from the process, for example withdrawn from the trimerisation zone or from the hydrotreatment zone.

In the trimerisation zone a gas feed may be present, where the gas may be a selected from the list consisting of:

nitrogen, carbon dioxide, water vapour, methane and/or hydrogen; such as nitrogen, carbon dioxide or hydrogen, preferably hydrogen.

In the process, the trimerisation product may be isolated in a fraction having a boiling point of more than 380° C., such as more than 450° C. The process may further comprise a step c) isomerising the hydrotreated base oil product. A base oil composition is obtainable according to the process described.

A base oil composition as described herein may be used for improving the lubricating properties of base oil.

BRIEF DESCRIPTION OF DRAWINGS

FIG. 1 shows examples of poly-alpha-olefins from 1-decene

FIG. 2 shows a exemplary reaction scheme for producing a trimer.

FIG. 3 shows trimerised palmitic acid, a saturated $C_{16}$ fatty acid.

FIG. 4 shows trimerised palm fatty acid distillate (PFAD), a mixture comprising saturated $C_{16}$ and $C_{18}$ fatty acids.

FIG. 5 shows trimers as a function of fatty acid conversion. It can be seen that the higher the conversion of the palmitic acid feed (C16FA), the more the trimer content increase.

FIG. 6 shows an expanded view of FIG. 5, where it can be seen that for each of the individual reaction conditions, the trimer content of the product increases with increasing fatty acid conversion, and that more than 5 wt % trimers may be formed when it is ensured that the fatty acid conversion is 99.5% or higher.

FIG. 7 shows a fraction of trimerised palmitic acid that boils above 450° C., where it can be seen that the major product is a $C_{47}$ paraffinic product, which has been identified by analysis to be a compound of formula I.

FIG. 8 shows a fraction of trimerised palmitic acid that boils between 380 and 450° C., where it can be seen that the major product is a $C_{31}$ paraffinic product, which has been identified by analysis to be a product arising from dimerization of the fatty acids by ketonisation.

FIG. 9 shows the effect of the amount in % of trimerised product (x-axis) on the improvement of the viscosity index (y-axis)

DETAILED DESCRIPTION OF THE INVENTION

In describing the embodiments of the invention specific terminology will be resorted to for the sake of clarity. However, the invention is not intended to be limited to the specific terms so selected, and it is understood that each specific term includes all technical equivalents which operate in a similar manner to accomplish a similar purpose.

While the benefits of the invention have in some instances been described with reference to engine oil for simplification of the discussion, the benefits of the invention are not limited to engine oils.

Base oils for passenger car engines may consist of e.g. 85-90% base oil and 10-15% of a performance enhancing additive package. Since the base oil is typically the largest component in passenger car engines, it has a dramatic effect on the performance of the fluid. The base oil affects many parameters such as the viscosity, oxidation stability, volatility, viscosity index, as well as cold flow properties such as pour point and/or cloud point.

Performance enhancing additive packages may include different additives, such as for example friction modifiers, viscosity modifiers and pour point depressants.

The American Petroleum Institute (API) divides base oils into five main groups. Groups I-III are petroleum base oil of varying qualities.

TABLE 1

| API base stock categories | | | |
|---|---|---|---|
| Group | Sulfur, wt-% | Saturates,% | Viscosity Index (VI) |
| I | >0.03 and/or | <90 | 80-119 |
| II | ≤0.03 and | ≥90 | 80-119 |
| III | ≤0.03 and | ≥90 | ≥120 |
| IV | Synthetic poly-alpha-olefins (PAOs) | | |
| V | Any other type of base oil than group I-IV | | |

The API defines the differences between Group II and III only in terms of the viscosity index (VI), and the Group III base oils are also called very high viscosity base oils (VHVI). However, also cold flow properties as well as Noack volatility number are important characteristics of base oils.

Oil volatility is commonly measured using the Noack volatility test (for example ASTM D5800 or CECL-40-93-B). Prior to the Noack test a lubricant's flash point was used to approximate the oil's volatility. In the Noack test, an oil sample is weighed and heated to 250° C. for one hour (250° C. is intended to simulate upper engine temperatures). Dry air is passed over the sample, carrying the oil vapours that have boiled off and depositing them in a beaker. The original sample is removed and re-weighed. Any reduction in weight is reported as a percentage lost of the original weight. The Noack volatility limit in % weight loss (g/100 g) as measured using ASTM D5800 has to meet standards. The API SN performance classification for example require weight loss due to volatility to be no greater than 15% for all viscosity grades of motor oil. The lower the Noack number the better, as it is a measure of evaporation of the lightweight molecules in the oil evaporating more readily when exposed to high temperatures, which will reduce the oil level. Low Noack number oils, which resist volatility better can reduce oil consumption and thereby maximise engine performance, when used as engine oil. Most conventional passenger car engine oils of 2016 will typically have Noack numbers of >13% while synthetic passenger car engine oils might be about 9-11%. Full synthetic heavy duty oil can have Noack numbers down to 8-9%.

For base oils, typically it is observed that the higher the boiling range temperature, the higher the viscosity, and the lower the oil volatility. Conversely, it is typically also observed that a lower viscosity is connected to a higher oil volatility.

The higher the oil volatility, the more engine oil evaporates and in turn the heavier the oil becomes. Heavier, more viscous oils circulate poorly, which affects fuel economy, oil consumptions and emissions.

Low temperature cranking is measured by the Cold Crank Simulator (CCS) at low temperature, such as for example −30° C. and the value is given in centipoise (cP), which is the same as millipascal-second (mPa*s). It is a test that simulates the action of a starter motor on an engine. The test is important because it is related to the resistance that the battery and starter motor experience when producing an adequate cranking speed at low temperatures, when for example starting an engine during winter time.

The SAE low temperature viscosity requirements relating to cranking specifies that for the 0W SAE viscosity grade, the maximum allowed cranking is 3250 cP at −30° C. (the lower the value the better).

A number of different branched hydrocarbon compounds (formula I) having a star-shaped configuration (S) are prepared from renewable oils containing fatty acids or derivatives containing fatty acids. The branched hydrocarbon compounds may be isolated individually or in mixtures, and may be used as part of base oils, in particular renewable base oils (RBOs). The process for preparing the branched hydrocarbon compounds of formula I involve conditions that favour a trimerisation reaction followed by hydrotreating conditions. The compounds of formula I may be made by catalytically treating renewable material containing fatty acids in some form (e.g. free fatty acids or fatty acid containing derivatives, such as triglycerides or other esters) in a process, and the compounds have desirable qualities relating to lubrication, cold flow as well as having a low Noack volatility.

Base Oil Compounds

Novel base oil compounds of the poly-alpha-olefin type (PAOs) with star-shaped configuration (S) have been manufactured. The compounds of formula I may be isolated individually or in mixtures. The novel base oil compounds may be prepared from renewable feed material containing fatty acids, and as such the novel base oil compounds may be considered as renewable base oil compounds. The base oil compounds of the poly-alpha-olefin type (PAOs) with star-shaped configuration (S) manufactured according to the processes of the present invention result in one or more properties selected from good lubricity properties, such as a high viscosity index, good cold flow properties, such as low cloud point and or pour point, and low Noack volatility.

The base oil compounds have a structure of the compounds of formula I:

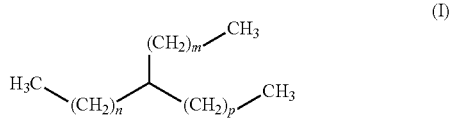
(I)

The compound of Markush formula I is a hydrocarbon, and in formula I, n, m and p may independently of each other be an integer value of 7 or higher, such as between 7 and 41. For example the integer values for n, m and p may be between 9 and 41 in order to emphasise the branching being of a star-shaped configuration (S) compared to e.g. a highly branched (HB) compound or a linear (L) compound (see FIG. 1), as well as linear compound that has been isomerised, which predominantly generates methyl branches. The compounds of the present invention may be obtained from trimerisation reactions of fatty acid containing material, and the integer values for n, m and p may independently of each other be 25 or lower to focus more on the length of fatty acids often encountered in renewable oils. For example the integer values for n, m and p may be between 7 and 41, for example between 7 and 25, for example between 9 and 41, for example between 9 and 25.

The total carbon number of formula I is 26 or above. In mineral oil refining it is usually the fraction containing compounds with 26 to 40 carbon atoms that is used for the creation of lubricating oils. The heaviest and largest of the hydrocarbons having carbon numbers over 40 are taken and usually used in asphalt-based products. The compounds of formula I may have at least 40 carbon atoms, for example more than 40 carbon atoms, such as 45 carbon atoms or more, for example 47 carbon atoms or more. For example a compound of formula I having 47, 53 or even 65 carbon atoms may be prepared using the process described herein starting from a $C_{16}$-, a $C_{18}$- or a $C_{22}$-fatty acid, respectively. The upper limit for the carbon numbers of formula I is not precisely defined. The upper limit for the carbon numbers may be 65, which would correspond to the trimer of Erucic acid ($C_{22}$-fatty acid), which may be found in a number of renewable oils, such as rapeseed oil, in particular in high erucic rapeseed oil.

The total carbon number of formula I may be 31 or above, which corresponds trimer compounds obtained from e.g. mixtures of lauric, decanoic and caprylic acid ($C_{12}$, $C_{10}$ and $C_8$-fatty acids), which may be found in a number of renewable oils, such as coconut oil, which typically contains a high amount of lauric acid.

For example the total carbon number of formula I may for example be between 31 and 65.

The compounds of Markush formula I may advantageously be obtained from renewable oils containing fatty acids, esters or triglycerides thereof. By renewable oils are considered oils collected from resources, which are naturally replenished on a human time scale, as opposed to fossil oils. Most fatty acids of plant or animal origin are straight-chain compounds, which most frequently contain an even number of carbon atoms, and usually no or only trace amounts of odd-numbered fatty acids. In respect to the compounds of formula I, should they be manufactured from fatty acids obtained from renewable oils having fatty acids with an even number of carbon atoms, the integer values for n, m and p would be odd numbered integer values. For example 7, 9, 11, 13, 15, 17, 19, 21, 23, 25, 27, 29, 31, 33, 35, 37, 39, 41; such as for example 9, 11, 13, 15, 17, 19, 21, 23, 25, 27, 29, 31, 33, 35, 37, 39, 41; for example 9, 11, 13, 15, 17, 19, 21, 23, 25.

The selection of n, m and p of formula I may be subject to one or more provisos, for example one or more of the below mentioned provisos in combination with the integer values for n, m and p being odd numbered integer values as described above.

The one or more provisos may be selected from 1, 2 or 3 of the following provisos.
with the proviso that when n and m are both 7, then p is not 9;
with the proviso that when n and m are both 9, then p is not 9 or 11,
with the proviso that n, m and p are not all 11.

Further provisos may be selected to focus more clearly on the compounds of formula I made according to the process of the present invention and using renewable oils described herein.

For example n, m and p may independently of each other be an odd numbered integer value between 7 and 41, where the total carbon number of formula I is between 26 and 65, with the proviso that when n and m are both 7, then p is not 9; with the proviso that when n and m are both 9, then p is not 9 or 11, and with the proviso that n, m and p are not all 11.

For example n, m and p may independently of each other be an odd numbered integer value between 9 and 41, where the total carbon number of formula I is between 31 and 65, with the proviso that when n and m are both 9, then p is not 9 or 11, and with the proviso that n, m and p are not all 11.

For example n, m and p may independently of each other be an odd numbered integer value between 7 and 25, where the total carbon number of formula I is between 31 and 65, with the proviso that when n and m are both 7, then p is not 9; with the proviso that when n and m are both 9, then p is not 9 or 11, and with the proviso that n, m and p are not all 11.

The selection of n, m and p of formula I may be where n is 13 or 15; m and p are independently of each other either 15 or 17. These compounds of formula I may for example be obtained by trimerising a mixture containing $C_{16}$- and $C_{18}$-fatty acids using the processes of the present invention, see compounds 1-6 of table 2, below.

A compound of formula I may also be where n is 13; m and p are both 15. This compound may be prepared exclusively from $C_{16}$ fatty acids (see compound 1 of table 2, below).

In the same manner, a compound of formula I may also be where n is 15; m and p are both 17. This compound may be prepared exclusively from $C_{18}$ fatty acids (see compound 2 of table 2, below).

The following specific compounds in table 2 may for example be prepared according to the invention. Reference is also made to FIG. 4 which shows a peak of trimerised product containing $C_{47}$-$C_{53}$ carbon products.

TABLE 2 compounds of formula I

| Compound | n | m | p | may be prepared from |
|---|---|---|---|---|
| 1 | 13 | 15 | 15 | $C_{16}$-fatty acids |
| 2 | 15 | 17 | 17 | $C_{18}$-fatty acids |
| 3 | 13 | 17 | 17 | mixture of $C_{16}$- and $C_{18}$-fatty acids |
| 4 | 15 | 15 | 17 | mixture of $C_{16}$- and $C_{18}$-fatty acids |
| 5 | 13 | 15 | 17 | mixture of $C_{16}$- and $C_{18}$-fatty acids |
| 6 | 15 | 15 | 15 | mixture of $C_{16}$- and $C_{18}$-fatty acids |

The novel compounds described above with a star-shaped orientation has good lubricity properties, including a high viscosity index. Additionally, it was found that novel intermediate compounds of formula II could be prepared.

The intermediate compounds of formula II and in turn the compounds of formula I may be formed from one or more trimerisation reactions (see FIG. 2).

For example Formula II may be prepared by one such trimerisation reaction scheme where two fatty acids react in at least two steps to form a compound of formula II. One such sequence of the two steps may involve reacting two fatty acids under ketonisation conditions leading to a ketone and a condensation reaction, where one of the alpha-carbon atoms of the ketone reacts with a fatty acid to form intermediate compounds of the formula II,

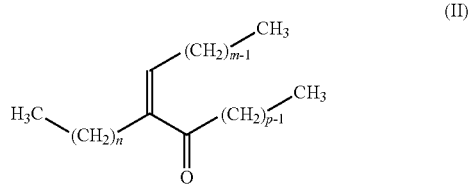

(II)

where n, m and p are independently of each other an integer value of 7 or higher, such as between 7 and 41, e.g.

between 9 and 41 or 9 and 25, and where the total carbon number of formula II is 26 or above, for example 31 or above, such as between 31 and 65.

For example intermediate compounds of formula II may be where n, m and p are independently of each other an integer value between 9 and 41, and where the total carbon number of formula I is between 31 and 65.

In addition to the specifically mentioned n, m and p values for formula II, the n, m and p of formula II may also be selected as described for formula I.

The selection of n, m and p of formula II may be where n is 13 or 15; m and p are independently of each other either 15 or 17.

TABLE 3 compounds of formula II

| Compound | n | m | p | may be prepared from |
|---|---|---|---|---|
| 7 | 13 | 15 | 15 | $C_{16}$-fatty acids |
| 8 | 15 | 17 | 17 | $C_{18}$-fatty acids |
| 9 | 15 | 15 | 17 | mixture of $C_{16}$- and $C_{18}$-fatty acids |
| 10 | 13 | 17 | 17 | mixture of $C_{16}$- and $C_{18}$-fatty acids |
| 11 | 15 | 17 | 15 | mixture of $C_{16}$- and $C_{18}$-fatty acids |
| 12 | 17 | 13 | 15 | mixture of $C_{16}$- and $C_{18}$-fatty acids |
| 13 | 15 | 15 | 15 | mixture of $C_{16}$- and $C_{18}$-fatty acids |
| 14 | 13 | 15 | 17 | mixture of $C_{16}$- and $C_{18}$-fatty acids |

Intermediate compound of formula II may undergo hydrotreatment in the form of hydrogenation reactions, such as double bond hydrogenation and hydrodeoxygenation to yield a compound of formula I.

The fatty acids used to prepare compounds of formula I or II may for example be $C_{16}$ fatty acids, $C_{18}$ fatty acids or mixtures thereof, or mixtures containing either $C_{16}$ fatty acids, $C_{18}$ fatty acids or both. Compound of formula II, where n is 13; m and p are both 15 may be prepared exclusively from $C_{16}$ fatty acids, and compounds of formula I, where n is 13; m and p are both 15 may be prepared exclusively from $C_{16}$ fatty acids (see compound 7 of table 3).

In the same manner, a compound of formula II may also be where n is 15; m and p are both 17. This compound may be prepared exclusively from $C_{18}$ fatty acids (see compound 8 of table 3).

The compounds of formula I may be isomerised to produce isomerised star-shaped compounds obtainable by subjecting one or more compounds of formula I to an isomerisation step. In the process for obtaining isomerised star-shaped compounds comprising between 1 to 5 methyl branches, less severe conditions during the isomerisation step, such as lower temperatures during the isomerisation step and/or less acidic catalyst material, may be employed in order avoid or reduce the amount of cracking, which may include cracking of the branches that give the compounds of formula I the star-shaped configuration (S). Reference is made to example 3 and table 6 showing an exemplary isomerisation catalyst and exemplary isomerisation conditions.

As shown in FIGS. 5 and 6, at least 2 wt % trimers are formed when it is ensured that the fatty acid conversion is 99.5% or higher, and as described for FIG. 6 that more than 5 wt % trimers may be formed when it is ensured that the fatty acid conversion is 99.5% or higher. Accordingly, the feed to the isomerisation step may comprise at least 2 wt %, preferably at least 5 wt % of one or more compounds of formula I.

The feed to the isomerisation step may comprise at least 80 wt % hydrocarbons, for example it may consist essentially of hydrocarbons.

The compounds of formula I may be separated from other components, e.g. by fractionation to provide a higher concentration of the compounds of formula I to the isomerisation step. For example feed may consist of at least 80 wt % hydrocarbons and comprise at least 15 wt %, at least 20 wt %, at least 32 wt %, such as at least 50 wt % or even at least 80 wt % of the compounds of formula I, such as one or more compounds of formula I wherein n, m and p are independently of each other an odd numbered integer value between 9 and 41, and where the total carbon number of formula I is between 31 and 65, with the proviso that when n and m are both 9, then p is not 9 or 11, and with the proviso that n, m and p are not all 11.

The isomerised star-shaped compounds may comprise at least one methyl branch, such as at least two, or at least three methyl branches, for example between one to five methyl branches. It is advantageous to provide isomerisation conditions that avoid or reduce cracking as described above. Ethyl or higher branches may also be present. Below is an illustration of how an isomerised star-shaped compound could look like, when a compound of formula I has undergone isomerisation to generate four methyl branches. The branches are typically located in close proximity to the end of the carbon chains of the star-shaped compounds.

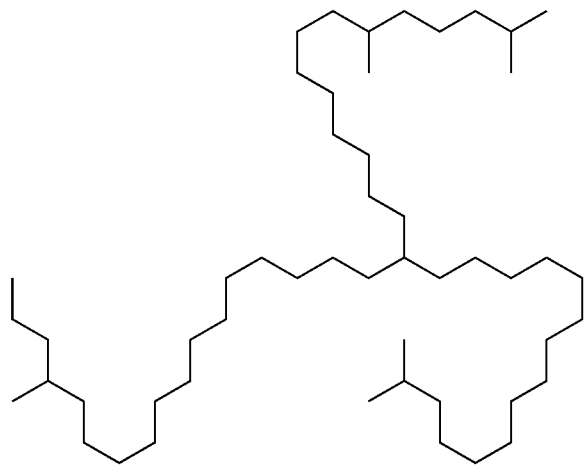 [SMILES: CCCC(C)CCCCCCCCCCCCCC(CCCCCCCCCCCCCC(C)C)CCCCCCCCC(C)CCCC(C)C]

Base Oil Mixtures

One or more compounds of formula I, and/or isomerised star-shaped compounds of formula I as described above may be present in a base oil mixture. The values for n, m and p may independently of each other be an integer value between 7 and 41 and the total carbon number of formula I may be between 31 and 65, or between 40 and 65, e.g. between 45 and 65, such as between 47 and 65. The values and ranges for carbon numbers as well as the n, m and p may be selected as described above for formula I.

For example the base oil mixture may comprise one or more compound(s) of formula I, wherein n, m and p are as described above for formula I. For example independently of each other an integer value, such as an odd numbered integer value, between 9 and 41, and where the total carbon number of formula I is between 31 and 65, or isomerised star polymers of formula I as described above.

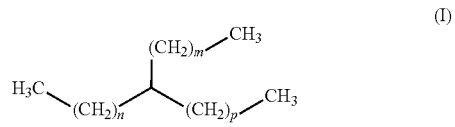

The base oil mixture may comprise more than two compounds of formula I and/or isomerised star-shaped compounds thereof, such as more than four or more than six compounds. Such a base oil mixture may contain one or more of compounds 1-6 of table 2.

For example the base oil mixture may comprise one or more compound(s) of formula I, wherein n is 13 or 15; m and p are independently of each other either 15 or 17, which are compounds 1-6 of table 2 above. The base oil mixture may comprise a compound of formula I, wherein n is 13; m and p are both 15, which is compound 1 of table 2 above, or the base oil mixture may comprise a compound of formula I, wherein n is 15; m and p are both 17, which is compound 2 of table 2 above.

The base oil mixture may be of a quality according to one of group I-V of the API base stock categories as shown in table 1. The base oil mixture may have 90% or more saturates and a viscosity index of 80 or higher, such as 120 or higher. The base oil mixtures may have a sulfur content of 0.03 wt % or lower. The base oil mixtures may have an oxygenate content of 5 wt % or lower, for example 1 wt % or lower or lower than 0.1 wt %. Additives later added to a base oil mixture prepared according to the present invention may contain oxygenates.

The base oil mixture may be a base oil stock, and it may be used for example in blends with other base oil stocks to provide a base oil stock with desired properties. The base oil mixture may also be finished base oil that can be directly used e.g. as an engine oil. When the base oil mixture is a finished base oil, usually an additive package is added to a base oil stock to modify the base oil stock, and to give the finished base oil the desired properties.

The base oil mixture may have a boiling point of 350° C. or more, such as 380° C. or more, such as 400° C. or more, such as 450° C. or more, such as 460° C. or more, for example 470° C. or more. The boiling point may be up to 730° C., for example up to 650° C., for example up to 620° C., for example up to 600° C., for example up to 550° C. For example the boiling point range of 380° C. to 730° C. was found in table 8 of example 4 to comprise a base oil mixture containing compounds of formula I, for example the boiling point range above 380° C., such as 380° C. to 730° C., and the boiling point range of 380° C. to 620° C. or to 550° C., in particular the boiling point range above 450° C., such as 470° C. to 730° C., and the boiling point range of 460° C. to 620° C. or to 550° C.

The initial boiling point (IBP/SP) and the final boiling point (FBP/EP) may be determined by distillation or by simulated distillation (Sim Dist) based on either ASTM D6352 or D2887). The range of boiling points may be calculated as between the initial boiling point (IBP/SP) and the final boiling point (FBP/EP) or between the initial boiling point (IBP/SP) and the 95% evaporation boiling point.

The base oil mixture may comprise at least 2%, for example at least 5%, such as at least 10% or more of the one or more compound(s) of formula I, measured as area-% using GC.

Processes for Base Oil Production

The base oils may be produced by a process for base oil production, comprising a) trimerising a feed comprising at least one fatty acid to provide a trimerisation product where a mixture of fatty acid trimers is obtained; and b) hydrotreating at least a portion of the trimerisation product to provide a base oil product; where the hydrotreated base oil product comprises one or more compound(s) of formula I, wherein n, m and p are independently of each other an integer value between 5 and 41, and where the total carbon number of formula I is between 19 and 65;

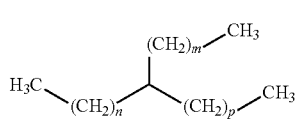
(I)

The process for base oil production involves one or more trimerisations reactions followed by a hydrotreatment step. The process produces a base oil, such as a base oil mixtures described herein, e.g. under the heading "base oil mixtures". The base oil produced according to the processes of the present invention may have very little oxygenates and saturates as a result of the hydrotreatment step. The amounts of oxygenates and saturates are described herein, e.g. under the heading "base oil mixtures". The process for base oil production may involve a step of providing a distillate in the base oil boiling point range, for example providing a distillate with a boiling point of 380° C. or above, for example as described above under the heading "base oil mixtures".

The process involves a step of trimerising a feed comprising at least one fatty acid. FIG. 2 shows an exemplary scheme for producing a trimer through trimerising a feed comprising at least one fatty acid, where the fatty acid is palmitic acid (C16:0). Without wishing to be bound by any theory, the inventors have found that the trimerising of the feed may occur through several possible reactions, where one example is given in FIG. 2. It has been found that starting from palmitic acid as the model feed, a ketone product may be obtained through a ketonisation reaction. Further it was found that under the trimerisation reaction, aldehydes were present in the processed feed. The aldehyde and dimerised ketone may react to form an aldol condensation product of formula II—a trimerisation product. Other mechanisms for obtaining an intermediate product of formula II are possible, such as for example an aldol condensation reaction followed by a ketonisation reaction. The trimerisation product may comprise one or more compound(s) of formula II, where n, m and p are independently of each other an integer value between 5 and 41, and where the total carbon number of formula II is between 25 and 65, or where n, m and p and the total carbon number have been selected as described above under the headings "base oil compounds" or "base oil mixtures".

The process uses a feed comprising at least one fatty acid. The at least one fatty acid may be selected from a $C_6$ or higher fatty acid, such as $C_7$ or higher, e.g. $C_8$ or higher, such as $C_9$ or higher. It may for example be a $C_{30}$ or lower fatty acid, such as $C_{26}$ or lower fatty acid or $C_{22}$ or lower fatty acid, for example the one or more fatty acid may have fatty acid(s) between a $C_7$ to $C_{22}$ fatty acid. The at least one fatty acid includes mixtures of fatty acids with different carbon numbers, and it also includes fatty acids as fatty acid derivatives having a carboxylic acid moiety, such as fatty acid esters or triglycerides of fatty acids. The at least one fatty acid do not have to be linear, and may be branched or include ring structures. It is preferred that the at least one fatty acid comprises a fraction of linear/unbranched fatty acids, as such structures will more readily react to provide compounds for formula I. Most of the fatty acids contained in renewable oils comprise linear/unbranched fatty acids, typically as free fatty acids or as triglycerides of fatty acids, and also as free fatty acids. Renewable oils are oils that are replenished on a human timescale, as opposed to fossil oils. As mentioned, the feed may comprise at least one fatty acid. Renewable oils may be plant derived oils or fats, animal oils or fats, and fish oil and fats or waste oil or fats. For example the feed may be selected from one or more of the list consisting of: palm oil, canola oil, rapeseed oil, olive oil, sunflower oil, beef fat, lard, coconut oil, corn oil, soybean oil, jatropha oil, tall oil, crude tall oil, tall oil pitch, tall oil heads, tall oil fatty acids or different fractions thereof, such as palm oil fatty acid distillate (PFAD) or waste oils, such as used cooking oil. The feed may comprise any fatty acid containing fraction of tall oil, and the term fatty acid also include e.g. resin acids of tall oil, which may have branchings and ring structures. Free fatty acid containing feeds are specifically suitable when the process includes the reaction between two free fatty acids.

In the case of feeds containing unsaturated fatty acids, a pre-hydrogenation step may be used prior to the trimerisation step to saturate any unsaturations, such as unsaturated fatty acids. Performing the trimerisation reactions with saturated feeds may avoid or at least significantly reduce the double bond isomerisation reactions that will form highly branched (HB) products, as shown in FIG. 1.

The trimerisation product obtained from the trimerisation step may comprise an intermediate product with the formula II as described above under the heading "Base oil compounds". It may be present together with other fatty acid trimers in a mixture of fatty acid trimers.

The trimerisation product may be isolated, or it may undergo other reactions in addition to the trimerisation reactions.

The process involves hydrotreating at least a portion of the trimerisation product to obtain a base oil product. The hydrotreatment is a catalytic hydrogenation reaction, wherein the trimerisation product is contacted with a hydrotreating catalyst and hydrogen. This results in a number of hydrogenation reactions, including double bond hydrogenation and hydrodeoxygenation reactions to produce a hydrotreated hydrocarbon base oil product.

The hydrotreated base oil product comprises one or more compound(s) of formula I, where n, m and p are independently of each other an integer value between 5 and 41, and where the total carbon number of formula I is between 25 and 65, or where n, m and p and the total carbon number have been selected as described above under the headings "base oil compounds" or "base oil mixtures".

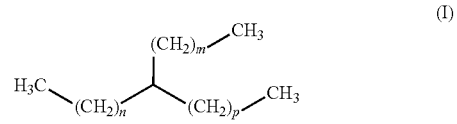
(I)

The process may be characterised in that the hydrotreated base oil product having a pour point lower than 5° C. The process may be further characterised in that the base oil comprises at least partly the trimerisation product of formula I. That is, when the trimerisation reaction followed by the hydrotreatment reaction is conducted it will prepare base oil mixtures comprising the star-shaped compounds of formula I, which improves the pour point of a hydrocarbon mixture, such as the base oil mixture obtained. The pour point is improved, e.g. with reference to linear hydrocarbons (L), which may be obtained through ketonisation reaction only.

The process may further comprise a step involving isomerising the hydrotreated base oil product. The pour point obtained prior to subjecting the base oil mixture to an optional isomerisation step, (which isomerisation step may or may not be present in the process), is 5° C. or lower, such as 0° C. or lower, for example −5° C. or lower. The isomerisation step further improves the pour point of the hydrotreated base oil product to −10° C. or lower, such as −20° C. or lower, for example −30° C. or lower, depending on the severity of the isomerisation step.

Isomerised star-shaped compounds may also be obtained in a combined hydrotreatment and isomerisation step using a suitable catalyst and suitable conditions, for example using a NiW catalyst, for example NiW on a support, such as alumina or NiW/zeolite on a support, e.g. alumina. That is, the process may involve a trimerisation step followed by a combined hydrotreatment and isomerisation step, wherein both hydrotreatment and isomerisation reactions occur.

The process may be characterised in that carbon atoms of one or more compound(s) of formula I exclusively come from monocarboxylic fatty acids. The monocarboxylic fatty acids may be in the form of free fatty acids or fatty acid derivatives containing the carboxylic acid moiety, such as fatty acid esters, e.g. triglycerides.

The process may be further characterised in that the trimerisation is carried out until 99.5% of the at least one fatty acids have been converted. For example the process may be further characterised in that the trimerisation is carried out at a conversion level of at least 99.5% of the at least one fatty acid of the feed, i.e. the conversion level is maintained at a high level, such as 99.6%, even 99.8% or 99.9% of the at least one fatty acids have been converted, measured as area-% using GC. During ketonisation reactions of the prior art, where fatty acids are dimerised and hydrodeoxygenated into linear hydrocarbon base oils (L), such ketonisation steps are usually run at a conversion rate of around 97% or less, as it is considered more efficient. It is not necessary to fully convert the fatty acids into a ketonisation product because the remaining fatty acids will be hydrotreated into n-paraffins and can be fractionated and used e.g. as a diesel product. Furthermore, it requires that for a given feed ketonisation parameters are modified so as to give a higher conversion rate.

The conversion may for example be manipulated to be at a level of 99.5% or higher in a continuous fixed bed reactor by manipulating in particular the temperature and the feed flow rate (WHSV), and to some extent also the pressure. In general the reaction temperature increases the reaction rate. Lower feed rate increases the residence time which typically gives higher conversion. The effect of pressure depends on the reaction chemistry. For example, if gaseous products or products lighter than the feed are formed during the reaction, a lower pressure may in some cases be advantageous so that these light products may be desorbed from catalyst active site to gas phase.

No individual parameter alone (temperature, pressure, WHSV, gas type or gas amount) facilitate the formation of trimerised product significantly, but rather the formation of the trimerised product is the result of the combination of suitable reaction condition parameters. A high conversion level of palmitic acid is required to be maintained, and may be achieved by the reaction condition parameters described herein. Only when the conversion level of over 99.5% is maintained, does the formation of the trimerised product increase unexpectedly as shown in example 2.

In particular, a higher conversion rate than 97% may require modification of the ketonisation parameters, such as the hydrogen amount, the WHSV, the temperature and the pressure.

It was found by the inventors that providing ketonisation conditions that ensured a conversion rate of the at least one fatty acids to 99.5% or above resulted in an amount of 2 wt % or more of trimerisation product as evident from FIGS. 5 and 6.

The process may be further characterised in that the trimerisation is carried out until at least 2 wt % trimer product has been formed, such as for example at least 5 wt % trimer product. Adjusting the parameters such as hydrogen amount, WHSV, temperature and pressure allows for the production of between 2 wt % and 20 wt % of trimerised product.

The conversion of the at least one fatty acids, and the formation of 2 wt % or more of trimerised product may be monitored using GC as described in the examples.

The process may further under the trimerising step a) comprise contacting the at least one fatty acid with a trimerisation catalyst in a trimerisation zone under trimerisation conditions to provide the mixture of fatty acid trimers; and step b) comprises contacting the mixture of fatty acid trimers with a hydrotreating catalyst in the presence of hydrogen gas in a hydrotreating zone under hydrotreating conditions to provide the base oil product.

The trimerising under step a) of the process may comprise the formation of a ketone from a reaction between two fatty acids followed by a condensation reaction between the ketone and another fatty acid to produce an alpha-substituted and alpha-unsaturated ketone.

The trimerisation catalyst may comprise a catalyst selected from one or more of the list consisting of: Ti, Mn, Mg, Ca containing metal oxide catalyst; preferably the trimerisation catalyst is a Ti containing metal oxide catalyst. Metal oxides of Ti, Mn, Mg and Ca may be titanium oxide, manganese oxide, magnesium oxide or calcium oxide. This primary metal oxide may be combined with other metal oxides, such as metal oxides of alkali metals, e.g. Na, Li, K. When desiring to produce trimerised product the catalyst titanium dioxide together with a metal oxide of an alkali metal is preferred, for example a $TiO_2$ and $K_2O$. It is advantageous that the metal oxide has been prepared as a catalyst metal oxide. This may include a specific BET surface area, specific average pore diameters and crystallinity. For example the BET surface area may be above 40 $m^2/g$, such as from 40 to 200 $m^2/g$, for example between 45 and 100 $m^2/g$. The average pore diameter may be from 100 to 200 Å. The crystallinity of the metal oxide may for example be between 50 to 100%.

The trimerisation zone may be a reactor or one or more a catalyst bed(s) in a fixed bed reactor, which may hold the trimerisation catalyst.

If feed comprises triglycerides or other esters of fatty acids, it has been found that a trimerisation catalyst in combination with a certain amount of a hydrotreating catalyst can assist with the breaking of the ester bonds, but at the same time not fully convert the fatty acids to n-paraffins before they can undergo the trimerisation reaction. The trimerisation catalyst may be mixed with hydrotreating catalysts in the art, for example molybdenum or wolfram catalyst, typically on a support, such as $Al_2O_3$, which may or may not be promoted. Typical promoters are Ni and/or Co. Promoted hydrotreating catalysts may for example be NiMo, CoMo, NiW, CoW, NiCoMo. The hydrotreating catalyst may be present in an amount of up to 50 wt % of the total amount of catalysts, for example 25 wt % or less. It can be seen from table 8 that a feed containing 80% titanium dioxide catalyst and 20% NiMo effectively converted a feed of 30% palm fatty acid distillate (PFAD) and 70% purified palm oil, which contains triglycerides.

The trimerisation reaction conditions may comprise a temperature in the range from 300 to 400° C., a pressure in the range from 5 to 100 barg and a WHSV in the range from 0.1-5 $h^{-1}$, and where the trimerisation catalyst comprises a metal oxide catalyst. Adjusting these parameters within these ranges allows for the production of between 2 wt % and 20 wt % of trimerised product.

For example the temperature range may be 340° C. or higher. It may for example be between 300° C. and 370° C., such as between 340° C. and 365° C., between 345° C. and 365° C. or between 345° C. and 355° C.

For example the pressure range may be from 5 to 100 barg, such as from 5 to 30 barg. The WHSV may be in the range from 0.1-5 $h^{-1}$, for example between 0.5-2.5 $h^{-1}$, for example between 0.5-1.5 $h^{-1}$.

In the trimerisation zone a gas feed may be present, where the gas may be a selected from the list consisting of: nitrogen, carbon dioxide, water vapour, methane or hydrogen, preferably hydrogen. It was found that nitrogen gas addition compared to no gas increased the conversion the fatty acid containing feed. It was also found that changing the nitrogen gas with hydrogen gas further increased the conversion rate of the fatty acid containing feed, and at the same time also increased the trimer formation, see example 2.

For example the conversion level in a continuously operated fixed catalyst bed tube reactor may be maintained at above 99.5, such as around 99.7% by selecting hydrogen as inlet gas feed in an amount of from 4 to 6 l/h, in a reaction temperature of 340 to 360° C., at a reaction pressure from 8 to 15 barg and WHSV from 0.5 to 1.2 $h^{-1}$, while feeding a $C_{16}$ fatty acid containing feed, such as palmitic acid into the reactor. The amount of trimer product obtained is above 2 wt-%, preferably above 4 wt-%.

The mixture of fatty acid trimers is contacted with a hydrotreating catalyst. The hydrotreating catalyst may be typical hydrotreating catalysts in the art, for example it may comprise a hydrogenation metal on a support, such as for example a catalyst selected from a group consisting of Pd, Pt, Ni, Co, Mo, Ru, Rh, W or any combination of these. The hydrotreatment step is done under hydrotreating conditions to provide the base oil product. The hydrotreatment step may for example be conducted at a temperature of 100-500° C. and at a pressure of 10-150 barg. Examples of hydrotreatment conditions can be seen in example 3 and table 6. The hydrotreatment step may for example be conducted at a temperature of 250-350° C., at a pressure of between 30 and 80 barg, a WHSV of 0.5-2 $h^{-1}$, and a $H_2$/oil ratio of 500-1500 nl/l. Further in the process, the feed comprising at least one fatty acid may be diluted with a stream of hydrocarbons. The dilution may also occur once the trimerisation product has been produced, prior to the hydrotreatment step. The dilution may be 30 wt % hydrocarbons and 70 wt % trimerisation product, for example between 30-85 wt % hydrocarbon and 15-70 wt % trimerisation product. The stream of hydrocarbons used for dilution may in part or fully be product recycle.

The stream of hydrocarbons may be recycled product of the process, for example the ratio of feed comprising at least one fatty acid to recycled product of the process may be between 1:9 and 9:1. The product recycle may have undergone fractionation before being recycled, for example it may be the fraction boiling above 380° C. that is recycled, or any other fraction of the base oil mixture described herein. The amount of formula I in the base oil mixture obtained by the processes of the invention may increase when using product recycle as the stream of hydrocarbons used for dilution of the (fresh) feed. For example the product recycle may increase the amount of compound(s) of formula I in the base oil mixture to 5 wt % or more, such as 15 wt % or more, for example up to 32 wt % or more. When the trimerisation zone comprise more than one catalyst bed, the product recycle may be recycled to either of the catalyst beds, for example the product recycle may be recycled to the first catalyst bed of the trimerisation zone, the last bed of the trimerisation zone, or an intermediary bed of the trimerisation zone.

Any product withdrawn from the process may be recycled in the manner described above, for example the product withdrawn may be recycled to the first catalyst bed of the trimerisation zone, the last bed of the trimerisation zone, or an intermediary bed of the trimerisation zone. For example the ratio of feed comprising at least one fatty acid to any product withdrawn from the process may be between 1:9 and 9:1. For example the product may be withdrawn from the trimerisation zone or from the hydrotreatment zone. When these zones contain catalyst beds product may be withdrawn after the first catalyst bed, after the last bed, or after an intermediary bed of these zones.

The hydrotreatment catalyst may for example be a molybdenum or wolfram catalyst, typically on a support, such as $Al_2O_3$. The catalyst may or may not be promoted. Typical promoters are Ni and/or Co. Promoted hydrotreating catalysts may for example be NiMo, CoMo, NiW, CoW, NiCoMo. When a wolfram based catalyst is used, such as NiW catalysts it has the further advantage that it can also catalyse isomerisation reactions. The hydrotreatment is done in the presence of hydrogen gas in a in a hydrotreating zone, which may be a catalyst bed in a fixed bed reactor.

The process may be further characterised in that it either does or does not include a step for isomerising the trimerisation product.

The product of the hydrotreatment step may subjected to an isomerization step in the presence of hydrogen and an isomerization catalyst. Both the hydrotreatment step and isomerisation step may be conducted in the same reactor, and even in the same reactor bed.

The hydroisomerisation reaction may be in the presence of an isomerisation catalyst, such as a catalyst comprising a Group VIII metal, preferably Pt, and a molecular sieve, optionally on support. The support may for example be selected from silica, alumina, clays, titanium oxide, boron oxide, zirconia, which can be used alone or as a mixture, preferably silica and/or alumina. The molecular sieve may for example be zeolites, such as ZSM or aluminophosphate molecular sieves, such as SAPO, such as SAPO-11, MeAPO, MeAPSO, where Me is e.g. Fe, Mg, Mn, Co or Zn, or other elements (El) molecular sieves EIAPO or EIAPSO, e.g. silica-alumina, Y zeolite, SAPO-11, SAPO-41, ZSM-22, ferrierite, ZSM-23, ZSM-48, ZBM-30, IZM-1, COK-7. Suitable molecular sieves and characteristics of molecular sieves suitable for hydroisomerisation applications are known to the skilled person and have been described in the literature, such as in Handbook of heterogeneous catalysis from VCH Verlagsgesellschaft mbH with editiors Ertl, Knözinger and Weitkamp, volume 4, pages 2036-2037, which is hereby incorporated by reference herein.

The isomerisation catalyst may be a bifunctional catalyst comprising a noble metal such as Pt or Pd, or alternatively a non-noble metal or metal combination, such as NiW together with a molecular sieve. The molecular sieve may be a zeolite with medium (10 ring) or large pore (12 ring) sizes, for example SAPO molecular sieves, ZSM-5, ZSM-11, ZSM-12, ZSM-22, ZSM-23, ZSM-35, zeolite Y, Zeolite beta. The isomerisation catalyst may be a noble metal bifunctional catalyst such as a Pt containing commercial catalyst, for example Pt and a medium and/or large pore size molecular sieve or zeolite; Pd and a medium and/or large pore size molecular sieve or zeolite. For example Pt-SAPO or Pt-ZSM-catalyst or for example a non-noble catalyst, such as NiW alone or together with a molecular sieve as mentioned above, and optionally on a support. For example NiW/Al$_2$O$_3$, or NiW/zeolite/Al$_2$O$_3$. The hydrotreatment and isomerisation steps may be done in the same catalyst bed using e.g. the NiW catalyst in both the hydrotreatment and isomerisation step. The isomerization step may for example be conducted at a temperature of 200-400° C. and at a pressure of 20-150 barg. As explained elsewhere in this description, it is desirable to reduce the severity of the isomerisation reaction to avoid or reduce the amount of cracking of the star-shaped compounds, in particular cracking of the star-shaped compounds, which would completely remove the side branch making out part of the star-shape. The cracking side reaction is well-known in hydroisomerisation reactions. Conditions that reduce cracking will depend on the structure of the star-shaped compounds. The skilled person knows how to modify the severity of the isomerisation reaction by adjusting one or more of the reaction conditions (e.g. temperature, pressure, residence time and hydrogen to oil ratio) obtain isomerisation and reduce and/or avoid undesired cracking. For example the isomerisation step may be conducted in the presence of hydrogen and an isomerisation catalyst, such as a noble or non-noble isomerisation catalyst, at a temperature in the range of 250 to 400° C., a pressure in the range from 10 to 60 barg, and a WHSV in the range of 0.1-5 h$^{-1}$ and a H$_2$ flow of 100-800 nl H$_2$/l feed. Examples of isomerisation conditions can be seen in example 3 and table 6. The isomerisation step may for example be conducted at a temperature of 280-330° C., at a pressure of between 30 and 80 barg, a WHSV of 0.5-2 h$^{-1}$, and a H$_2$/oil ratio of 600-1200 nl/l. The isomerisation catalyst may be supported or on a support such as Al$_2$O$_3$, TiO$_2$, SiO$_2$, or combinations thereof.

The process may further involve isolation of the trimerisation product. For example the trimerisation product may be separated from a dimerisation product and isolated in a fraction that contains very little dimerization product, for example where the dimerization product is less than 5 wt-%, such as less than 1 wt-%. It is possible to analyse whether or not any particular fraction contains dimerised or trimerised product by using various techniques in the art, for example field ionisation mass spectrometry, see example 3 and FIGS. 7 and 8. For example the trimerisation product may be isolated in a fraction having a boiling point of more than 380° C., such as more than 450° C., for example more 460° C. or more, such as 470° C. or more, such as 480° C. or more, or for example 500° C. or more, such as the ranges described above under the heading "base oil mixtures".

According to the process described herein a base oil composition is obtained.

A base oil composition as described herein may be used for improving the lubricating properties of base oil, for example improving the viscosity index. The boiling point fraction above 450° C. from the trimerisation reaction and hydrotreatment reaction according to the process comprise the trimer product obtained from trimerisation of palmitic acid. It has a high viscosity index of 164, compared to the base oil fraction from 380-450° C. with a viscosity index of 155. As shown in FIG. 9 mixing in only 10% of the trimerised product into the base oil fraction from 380-450° C. increases the viscosity index to 160. This shows that the effect that the trimer-containing fraction has on the viscosity index is not linear.

Further specific examples showing the effect of different reaction conditions on the conversion rate of the feed and the resultant star-shaped compounds of formula I may be seen in the examples.

When describing the embodiments of the present invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

The terms "comprising", "comprise" and comprises herein are intended by the inventors to be optionally substitutable with the terms "consisting of", "consist of" and "consists of", respectively, in every instance.

EXAMPLES

Reactor

The catalytic reactor used was a continuous flow tube reactor with a fixed catalyst bed. The reactor system has two heated pressurised (1-2 barg) feed chambers, the weight of which can be measured. These feed chambers can be used for simultaneous feeding of two feeds or separately. It is possible to feed pressurised gas like H$_2$, N$_2$, CH$_4$, water vapour or CO$_2$ in to the reactor. The heating of the reactor is enabled using three electric heating blocks. The reactor heating accuracy is 1° C. The catalyst average temperature is determined by a measurement of varying temperature points. The pressure is controlled by an automatic pressure regulator. Gas/liquid separation occurs in the heated product chamber at atmospheric pressure.

Description of the GC Measurement Parameters (Area-%) and Apparatus

Conversion of fatty acid (area-%) is measured by gas chromatography, GC analysis (Agilent Technology 7890). The detector used was a flame ionisation detector (FID). The GC column was a CP/SILS column with the following dimensions: 10 m×250 µm×0.12 µm. The peaks of the chromatograms were identified by GC-MS. The accuracy of GC-FID analysis is at least 0.01 area-% and many cases even 0.001 area-%. Hydrocarbons are analysed using area-% values, which are typically close to wt-% values.

The conversion of fatty acid (X) can be calculated from the GC analysis of the product (fatty acid peak area-%) and feed (fatty acid peak area-%). The conversion is the measure, which tells how many % of the starting material, i.e. feed, is converted to something else, typically product molecules.

X=[Fatty acid (area-%) in feed)–fatty acid (area-%) in product)]/[Fatty acid (area-%) in feed]

Example 1—Preparing a Base Oil Comprising Trimers Using a Palmitic Acid Feed

A fixed bed reactor operated in continuous mode comprising a catalyst bed loaded with 20 g catalyst material ($K_2O/TiO_2$; BET 50-54 $m^2/g$; average pore size 100-200 Å; crystallinity 50-100%) was used for the trimerisation reactions, where temperature, dilution and conversion rate of the feed is varied.

These experiments were done in order to see the effect of the dilution agent on the formation of the trimeric compounds. It was first concluded that dilution facilitates the formation of trimers, but when the conversion level was dropped to 87.1% well below 99.5%, it was seen that the formation of trimers were the typical level of below 2%.

From table 4 (below) it can be seen that when the palmitic acid conversion was maintained above 99.5 area-% (as measured by GC) the amount of trimer compounds according to formula II was from 8 to 15 area-% (see table 4, column 4A, 4B and 4C).

Comparing column 4A with 4B it can be seen that the diluent under the particular conversion conditions decreased the formation the trimer product from 9.9% to 8.2%.

Comparing column 4B with 4C it was seen that a lower temperature and lower WHSV also resulted in a fatty acid conversion of 99.5% and increased the yield of the trimer product from 8.2% to 14.7%.

Comparing column 4C with 4D it was seen that the lower temperature required also a lower WHSV in order to get a satisfactory conversion and more than 2.0% trimerised product.

The GC distillation for trimerised palmitic acid showing the $C_{47}$ peak is shown in FIG. 3.

TABLE 4 base oil mixture containing trimer product from palmitic acid

| | | 4A | 4B | 4C | 4D |
|---|---|---|---|---|---|
| Feed | | | | | |
| Hydrogen | l/h | 5.5 | 5.5 | 5.5 | 5.5 |
| Pressure | barg | 9.8 | 10.2 | 10.1 | 9.9 |
| Temperature | ° C. | 360 | 360 | 350 | 350 |
| WHSV | $h^{-1}$ | 1.0 | 1.0 | 0.5 | 1.0 |
| Dilution | | 0 | 1:1 | 1:1 | 1:1 |
| Fatty acid conversion | area-% | 99.6% | 99.9% | 99.9% | 87.1% |
| Mass balance | | | | | |
| Vapour phase | wt-% | 8.7% | 3.9% | 5.7% | 2.8% |
| Aqueous phase | wt-% | 3.3% | 3.0% | 2.9% | 1.7% |
| Organic phase | wt-% | 88.0% | 93.1% | 91.4% | 95.5% |
| Composition of organic phase | | | | | |
| Unconverted fatty acid | area-% | 0.4% | 0.1% | 0.1% | 12.9% |
| Others | area-% | 4.2% | 9.6% | 10.5% | 12.5% |
| Ketone dimer | area-% | 72.5% | 73.8% | 61.5% | 68.4% |
| Trimer product ($C_{47}$) | area-% | 9.9% | 8.2% | 14.7% | 1.2% |
| Heavies | area-% | 1.0% | 1.4% | 4.6% | 0.5% |

The feed is Palmitic acid (C16:0 fatty acid). The dilution is made using $C_{15}$-$C_{18}$ n-paraffins obtained from hydrodeoxygenation of animal fat. An aqueous phase is separated from an organic phase and both phases are weighed separately. The vapour phase is calculated as weight of feed minus the weights of the aqueous and organic phases. The composition of the organic phase is measured using GC, and the sum of the area-% of the organic phase is normalised to the weight percent of the organic phase.

Example 2—Effect of Various Parameters on the Trimerisation Product Yield

A fixed bed reactor as described under the heading "Reactor" with a palmitic acid feed was subjected to various parameters to evaluate the effect on the trimerisation product yield. In table 5, the mass balance and composition of organic phase is measured and calculated as described in example 1.

Comparing column 5A with 5B it can be seen that a lower WHSV (0.5 vs 1.0 $h^{-1}$) increase the palmitic acid conversion to 99.9% and at the same time an increase the formation of the trimerisation product to 2.2%.

Comparing column 5A with 5C it can be seen that the conversion of palmitic acid is increased significantly by nitrogen gas addition compared to no gas addition. At a conversion of 88%, the formation of the trimers is affected only some extent.

Comparing column 5C with 5D it can be seen that the pressure decrease from 25 barg to 10 barg significantly increased the conversion of palmitic acid. However, the formation of the trimeric product is not affected at the conversion level of 97.5%.

Comparing column 5D with 5E it can be seen that the change of nitrogen gas to hydrogen gas increased the conversion of palmitic acid from 97.5% to 99.9% and significantly affected the formation of the trimers (0.5% to 5.6%).

Comparing column 5E with 5F it can be seen that when WHSV was increased from 1.0 $h^{-1}$ to 2.0 $h^{-1}$, the conversion drop significantly and also the formation of trimers drop back to level 1.2%

Comparing column 5F with 5G it can be seen that when the pressure was then lowered from 10 barg to 2 barg once again conversion was increased significantly. However, the formation of trimers was only some extent affected.

Comparing column 5D with 5H it can be seen that the temperature decrease from 360° C. to 350° C. significantly decreased the conversion from 97.5% to 74.6%.

At the same time the formation of trimerised product increased rather significantly from 0.5% to 0.9% (80% increase), however, the trimerised product stayed below 1%.

Comparing column 5D with 5I it can be seen that change from nitrogen gas to $CO_2$ increased the conversion of palmitic acid some extent (from 97.5% to 99.4%), and increased the formation of the trimerised product significantly (from 0.5% to 1.6%). However, the trimerised product stayed below 2.0%.

Comparing column 5E with 5I it can be seen that the change of hydrogen gas to $CO_2$ affected the conversion of palmitic acid to some extent (from 99.9% to 99.4%), but significantly lowered the formation of the trimers (from 5.6% to 1.6%).

Comparing column 5J, 5K and 5L it can be seen that the change in the gas amount added from 5.0 l/h to 2.5 l/h and to 7.5 l/h does not influence the formation of trimerisation product significantly, but influences the conversion rate in that the conversion rate is decreased with decreasing amount of gas added.

Comparing column 5L with 5M it can be seen that the pressure change from 10 barg to 18 barg decreased to some extent the conversion of palmitic acid but did not alter much the formation of the trimers.

Comparing column 5M with 5N it can be seen that the WHSV decrease from 1.1 $h^{-1}$ to 0.6 $h^{-1}$ increased the conversion to some extent (from 96.1% to 99.7%), and at the same time increased significantly the formation of trimers from 0.7% to 9.1%.

It may be concluded from the results in table 5 that no individual parameter alone (temperature, pressure, WHSV, gas type or gas amount) facilitates the formation of trimers significantly, but rather that it is the result of the combination of suitable reaction condition parameters. A high conversion level of palmitic acid is required to be maintained, and may be achieved by these reaction condition parameters. Only when the conversion level of over 99.5% is maintained, does the formation of the trimerised product increase unexpectedly as shown by the FIGS. 5 and 6.

TABLE 5

Effect of gas and gas type

|  |  | 5A | 5B | 5C | 5D | 5E | 5F | 5G |
|---|---|---|---|---|---|---|---|---|
| Feed |  |  |  |  |  |  |  |  |
| Gas, amount | l/h | none | none | $N_2$, 5 | $N_2$, 5 | $H_2$, 5 | $H_2$, 5 | $H_2$, 5 |
| Pressure | barg | 25 | 25 | 25 | 10 | 10 | 10 | 2 |
| Temperature | °C. | 360 | 360 | 360 | 360 | 360 | 360 | 360 |
| WHSV | $h^{-1}$ | 1.0 | 0.5 | 1.0 | 1.0 | 1.0 | 2.0 | 2.0 |
| Dilution |  | 0 | 0 | 0 | 0 | 0 | 0 | 0 |
| Fatty acid conversion | area-% | 68.4% | 99.9% | 88.0% | 97.5% | 99.9% | 69.6% | 89.3% |
| Mass balance |  |  |  |  |  |  |  |  |
| Vapour phase | wt-% | 4.5% | 8.5% | 6.4% | 8.6% | 7.8% | 4.9% | 5.2% |
| Aqueous phase | wt-% | 1.9% | 2.0% | 1.9% | 2.5% | 3.4% | 1.3% | 2.7% |
| Organic phase | wt-% | 93.6% | 89.5% | 91.7% | 88.9% | 88.8% | 93.8% | 92.1% |
| Composition of organic phase |  |  |  |  |  |  |  |  |
| Unconverted fatty acid | area-% | 31.6% | 0.1% | 12.0% | 2.5% | 0.1% | 30.4% | 10.7% |
| Others | area-% | 3.5% | 6.5% | 3.5% | 3.0% | 2.9% | 4.3% | 3.2% |
| Ketone dimer | area-% | 58.2% | 80.6% | 75.6% | 82.8% | 79.9% | 57.8% | 76.6% |
| Trimer product ($C_{47}$) | area-% | 0.3% | 2.2% | 0.5% | 0.5% | 5.6% | 1.2% | 1.3% |
| Heavies | area-% | 0.0% | 0.1% | 0.1% | 0.1% | 0.3% | 0.1% | 0.3% |
| Dimer/trimer ratio |  | 225 | 36 | 148 | 162 | 14 | 49 | 59 |

|  |  | 5H | 5I | 5J | 5K | 5L | 5M | 5N |
|---|---|---|---|---|---|---|---|---|
| Feed |  |  |  |  |  |  |  |  |
| Gas, amount | l/h | $N_2$, 5 | $CO_2$, 5 | $CO_2$, 5 | $CO_2$, 2.5 | $CO_2$, 7.5 | $CO_2$, 7.5 | $CO_2$, 7.5 |
| Pressure | barg | 10 | 10 | 10 | 10 | 10 | 18 | 18 |
| Temperature | °C. | 350 | 360 | 360 | 360 | 360 | 360 | 360 |
| WHSV | $h^{-1}$ | 1.0 | 1.0 | 1.0 | 1.1 | 1.1 | 1.1 | 0.6 |
| Dilution |  | 0 | 0 | 0 | 0 | 0 | 0 | 0 |
| Fatty acid conversion | area-% | 74.6% | 99.4% | 95.8% | 88.1% | 98.6% | 96.1% | 99.7% |
| Mass balance |  |  |  |  |  |  |  |  |
| Vapour phase | wt-% | 6.0% | 8.2% | 5.7% | 7.1% | 7.5% | 7.3% | 7.4% |
| Aqueous phase | wt-% | 2.1% | 3.4% | 4.9% | 2.2% | 3.1% | 3.0% | 2.1% |
| Organic phase | wt-% | 91.9% | 88.4% | 89.4% | 90.7% | 89.4% | 89.7% | 90.5% |
| Composition of organic phase |  |  |  |  |  |  |  |  |
| Unconverted fatty acid | area-% | 25.4% | 0.6% | 4.2% | 11.9% | 1.5% | 3.9% | 0.3% |
| Others | area-% | 2.0% | 2.8% | 2.4% | 2.5% | 2.8% | 3.0% | 4.8% |
| Ketone dimer | area-% | 63.1% | 83.3% | 82.0% | 75.5% | 84.2% | 82.0% | 74.6% |
| Trimer product ($C_{47}$) | area-% | 0.9% | 1.6% | 0.7% | 0.6% | 0.8% | 0.7% | 9.1% |
| Heavies | area-% | 0.5% | 0.1% | 0.1% | 0.2% | 0.1% | 0.1% | 1.7% |
| Dimer/trimer ratio |  | 255 | 36 | 148 | 162 | 14 | 49 | 59 |

Example 3—Producing Renewable Base Oil (RBO)

A renewable base oil product was obtained by trimerisation, hydrotreatment and isomerisation in three separate units under the conditions shown in table 6. The feed was palmitic acid and in the trimerisation unit the conversion of the feed was 100%. The dilution was made using $C_{15}$-$C_{18}$ n-paraffins. After the hydrotreatment the dilution agent was removed by distillation prior to the isomerisation step.

TABLE 6

Renewable base oil (RBO) production conditions

|  |  | Trimerisation | Hydrotreatment | Isomerisation |
|---|---|---|---|---|
| Temperature | °C. | 360 | 290 | 312 and 318 |
| Pressure | barg | 25 | 40 | 50 |
| WHSV | $h^{-1}$ | 1 | 1 | 1 |
| $H_2$:Oil | nl/l | 1000 | 1000 | 800 |
| Dilution |  | 50:50 | 50:50 | no |
| Catalyst |  | $K_2O/TiO_2$ | NiMo/$Al_2O_3$ | Commercial Pt wax isomerisation catalyst |

TABLE 6-continued

Renewable base oil (RBO) production conditions

Base oil yield in wt-% based on undiluted feed

|  | >450° C. | 380-450° C. | >380° C. | Pour Point (>380° C. fraction) |
|---|---|---|---|---|
| Isomerised (312° C.) | 8 | 48 | 56 | −18° C. |
| Isomerised (318° C.) | 8 | 38 | 46 | −39° C. |

The yields of the different fractions (380-450° C. fraction and the >450° C. fraction) is shown based on the initial feed of fatty acids (undiluted feed). It can be seen that depending on the severity of the isomerisation step, the pour point can be modified to for example −18° C. or −39° C., which are excellent pour points for a unadditited base oil product (a base oil stock). It can also be seen that isomerisation conditions can be chosen so as to not detrimentally reduce the yield of the fraction containing the star-shaped compounds (the >450° C. fraction).

It can be seen from a field ionisation mass spectrometry (FIMS) analysis that the >450° C. fraction contains the trimer product (see table 7 and FIG. 7) in more than 30 wt % and that the 380-450° C. fraction contains a $C_{31}$ dimer product (see FIG. 8).

TABLE 7

FIMS analysis of palmitic acid based trimerisation product fraction (>450° C.)

|  | Total fraction ($C_{31}$-$C_{51}$) | $C_{47}$ fraction |
|---|---|---|
| Paraffins | 49.3% | 34.6% |
| Mono-naphthenes | 43.6% | 23.1% |

In table 8 (below) for the palmitic acid isomerised at 312° C., the fraction >450° C. comprises around 90% trimerised product with a small impurity of dimer product. The fraction 380-450° C. does not contain any trimerised product. The fraction >380° C. contains an estimated 10% trimerised product (see table 6). Plotting the estimated trimerised product amount in percent on the x-axis and the viscosity index on the y-axis in FIG. 9, it can be seen that the trimerised product improves the viscosity index from 155 to 160 by the addition of only 10% trimerised product, and that at around 90% trimerised product (the >450° C. fraction) the viscosity index is 164. Accordingly, there is not a linear relationship when adding the trimerised product to a base stock containing no trimerised product, and as little as 10% of trimerised product can have a significant increase on viscosity index.

TABLE 8

Properties of base oil end products

|  |  | >380° C. | 380-450° C. | >450° C. | >380° C.* | >450° C.** |
|---|---|---|---|---|---|---|
| Density | kg/m³ | 818 | 816 | 832 | 818 |  |
| Cloud point | ° C. | 1 | 0 | 12 | −16 |  |
| Pour point | ° C. | −18 | −21 | 0 | −39 | −18 |
| Viscosity (40° C.) | mm²/s | 19.6 | 17.6 | 45.8 | 18.4 | 88.9 |
| Viscosity (100° C.) | mm²/s | 4.6 | 4.3 | 8.5 | 4.3 | 13.0 |
| Viscosity Index |  | 160 | 155 | 164 | 147 | 144 |
| CCS −30° C. | mPas | 1310 | 1010 | 980 |  |  |
| Noack | wt-% | 6 | 7 | <6 | 7 | <17 |
| SimDist | SP ° C. | 384 | 381 | 447 | 373 | 458 |
|  | 5 ° C. | 420 | 414 | 462 | 391 | 483 |
|  | 10 ° C. | 431 | 427 | 494 | 400 | 505 |
|  | 30 ° C. | 442 | 437 | 545 | 428 | 543 |
|  | 50 ° C. | 448 | 441 | 551 | 440 | 561 |
|  | 70 ° C. | 451 | 445 | 556 | 446 | 579 |
|  | 90 ° C. | 528 | 448 | 593 | 494 | 622 |
|  | 95 ° C. | 544 | 450 | 607 | 540 | 643 |
|  | EP ° C. | 612 | 461 | 719 | 674 | 696 |

*base oil fraction of example 3 isomerised at 318° C.; the other three columns are base oil fractions isomerised at 312° C.
**base oil fraction of a feed (30 % palm oil fatty acid distillate and 70 % refined bleached and deodorized palm oil) that has undergone trimerisation, hydrotreatment and isomerisation (312° C. under the conditions described in table 6 above, with the exception that the trimerisation catalyst was 80 wt % $TiO_2$ and 20 wt % $NiMo/Al_2O_3$.

TABLE 7-continued

FIMS analysis of palmitic acid based trimerisation product fraction (>450° C.)

|  | Total fraction ($C_{31}$-$C_{51}$) | $C_{47}$ fraction |
|---|---|---|
| di-naphthenes | 6.6% | 3.5% |
| tri-naphthenes | 0.5% | 0.4% |
| Total | 100.0% | 61.6% |

Example 4—Properties of End Products

The different properties of the trimer containing base oil fraction was measured and shown in table 8 below. From the column containing the trimerised product (>450° C.) it can be seen that the viscosity index (VI) is 164 when palmitic acid is used as a feed, which is significantly higher than the minimum VI of 120 for Group III base oils.

The combined dimer and trimer fraction (>380° C.=380-450° C.+>450° C.) maintains a very high viscosity index of 160 and at the same time a good pour point of −18° C. The more severe isomerization conditions described in table 6 above resulted in the combined dimer and trimer fraction (>380° C.*) improving the pour point to −18° C. and still having a very high viscosity index of 147.

The density was measured using EN ISO 12185; Cloud point using ASTM D7689; Pour Point using ASTM D7346; Viscosity using EN ISO 3104; Viscosity index using ASTM D2270; CCS using ASTM D5293; Noack number using CECL-40-93-B; and SimDist AC750 using EN 15199-2.

The invention claimed is:

1. A compound of a formula I, wherein n, m and p are each, independently of each other, an odd numbered integer value between 9 and 41, and where a total carbon number of formula I is between 31 and 65, with a proviso that when n and m are both 9, then p is not 9 or 11, and with the proviso that n, m and p are not all 11

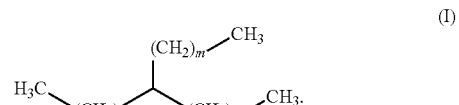

2. The compound according to claim 1, wherein n is 13 or 15; m and p are, independently of each other, either 15 or 17.

3. A process for obtaining isomerised star-shaped compounds containing any of between 1 to 5 methyl branches, the process comprising:

subjecting one or more compounds of formula I:

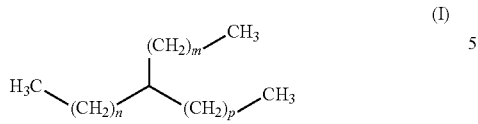

(I)

wherein n, m and p are each, independently of each other, an odd numbered integer value between 9 and 41, and where a total carbon number of formula I is between 31 and 65, with a proviso that when n and m are both 9, then p is not 9 or 11, and with a proviso that n, m and p are not all 11, to an isomerisation step; and conducting the isomerisation step in a presence of hydrogen and an isomerisation catalyst at a temperature in a range of 250 to 400° C., a pressure in a range from 10 to 60 barg a WHSV in a range of 0.1-5 $h^{-1}$, and a $H_2$ flow of 100-800 nl $H_2$/l feed.

4. A compound of a formula II, wherein n is 13; m and p are both 15:

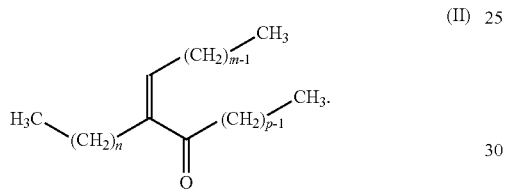

(II)

5. A base oil mixture comprising:
one or more compound(s) of formula I, wherein n, m and p are each, independently of each other, an odd numbered integer value between 9 and 41, and where a total carbon number of formula I is between 31 and 65:

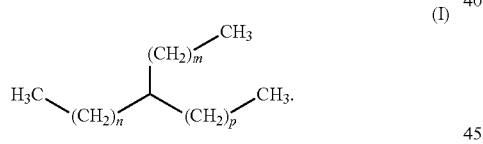

(I)

6. The base oil mixture according to claim 5, comprising:
one or more compound(s) of formula I, wherein n is 13 or 15; m and p are each, independently of each other, either 15 or 17.

7. The base oil mixture according to claim 5, wherein the base oil mixture is selected to have a boiling point of 380° C. or more, 450° C. or more, 460° C. or more, or 470° C. or more.

8. The base oil mixture according to claim 5, wherein the base oil mixture comprises:
at least 2% or more of the one or more compound(s) of formula I.

9. A process for base oil production, comprising:
a) trimerising a feed containing at least one fatty acid to provide a trimerisation product where a mixture of fatty acid trimers is obtained; and
b) hydrotreating at least a portion of the trimerisation product to provide a base oil product having a pour point lower than 5° C.;
where the hydrotreated base oil product includes one or more compound(s) of formula I, wherein n, m and p are each, independently of each other, an integer value between 9 and 41, and where a total carbon number of formula I is between 31 and 65;

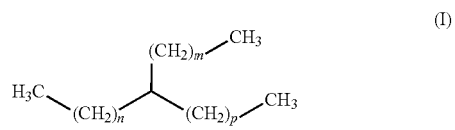

(I)

where carbon atoms of one or more compound(s) of formula I exclusively come from monocarboxylic fatty acids; and where the trimerising is carried out at a conversion level of at least 99.5% of the at least one fatty acid of the feed.

10. The process for base oil production according to claim 9, wherein step a) comprises:
contacting the at least one fatty acid with a trimerisation catalyst in a trimerisation zone under trimerisation conditions to provide the mixture of fatty acid trimers; and step b) comprises:
contacting the mixture of fatty acid trimers with a hydrotreating catalyst in a presence of hydrogen gas in a hydrotreating zone under hydrotreating conditions to provide the base oil product.

11. The process for base oil production according to claim 10, wherein the trimerisation conditions comprise:
a temperature in a range from 300 to 400° C., a pressure in a range from 5 to 100 barg and a WHSV in a range from 0.1-5 $h^{-1}$, and the trimerisation catalyst comprises:
a metal oxide catalyst.

12. The process for base oil production according to claim 9, wherein the trimerisation catalyst comprises at least one of:
a catalyst containing metal selected from one or more of a list consisting of: metal oxides containing Ti, Mn, Mg, and Ca; and
$TiO_2$ and one or more alkali metal oxides, where the one or more alkali metal oxides are selected from one or more of a list consisting of: metal oxides containing Li, Na, and K.

13. The process for base oil production according to claim 9, wherein the trimerising comprises:
formation of a ketone from a reaction between two fatty acids followed by a condensation reaction between the ketone and another fatty acid to produce an alpha-substituted and alpha-unsaturated ketone.

14. The process for base oil production according to claim 9, wherein the at least one fatty acid is selected from a $C_9$ to $C_{22}$ fatty acid.

15. The process for base oil production according to claim 9, the feed comprising at least one of:
at least one fatty acid selected from one or more of the list consisting of: palm oil, canola oil, rapeseed oil, olive oil, sunflower oil, beef fat, lard, coconut oil, corn oil, soybean oil, jatropha oil, tall oil, crude tall oil, tall oil pitch, tall oil heads and tall oil fatty acids; and
at least one fatty acid diluted with a stream of hydrocarbons, or where the trimerisation product is diluted with a stream of hydrocarbons.

16. The process for base oil production according to claim 10, wherein the feed comprises:
   at least one fatty acid diluted with a stream of product withdrawn from the process, for example or withdrawn from the trimerisation zone or from the hydrotreatment zone.

17. The process for base oil production according to claim 10, wherein in the trimerisation zone a gas feed is present, the gas being selected from the list consisting of: nitrogen, carbon dioxide, water vapour, methane and hydrogen.

18. The process for base oil production according to claim 9, wherein the trimerisation product is isolated in a fraction having a boiling point of more than 450° C.

19. The process for base oil production according to claim 9, comprising:
   c) isomerising the hydrotreated base oil product.

20. The base oil composition obtained by the process of claim 9.

21. A process according to claim 9, comprising:
   improving the lubricating properties of base oil with the hydrotreated base oil product.

22. A process for obtaining isomerised star-shaped compounds containing between 1 to 5 methyl branches, the method comprising:
   a feed containing at least 80 wt % hydrocarbons and at least 2 wt %, of one or more compounds of formula I:

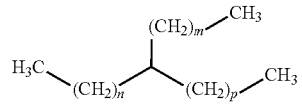

(I)

wherein n, m and p are each, independently of each other, an odd numbered integer value between 9 and 41, and where a total carbon number of formula I is between 31 and 65, with a proviso that when n and m are both 9, then p is not 9 or 11, and with a proviso that n, m and p are not all 11 to an isomerisation step; and
   conducting the isomerisation step in a presence of hydrogen and an isomerisation catalyst at a temperature in a range of 250 to 400° C., a pressure in a range from 10 to 60 barg a WHSV in a range of 0.1-5 $h^{-1}$, and a $H_2$ flow of 100-800 nl $H_2$/l feed.

23. The process according to claim 22, the feed being selected to comprise at least one of:
   at least 15 wt %, at least 20 wt %, at least 32 wt %, at least 50 wt % or at least 80 wt % of one or more compounds of formula I.

24. The process according to claim 22, wherein the feed consists essentially of hydrocarbons.

25. The process according to claim 24, wherein the feed consists essentially of hydrocarbons, and contains at least 15 wt % of one or more compounds of formula I.

* * * * *